(12) United States Patent
Kingston et al.

(10) Patent No.: US 8,383,420 B2
(45) Date of Patent: Feb. 26, 2013

(54) SOLID PHASE AND CATALYZED ENABLED AUTOMATED ISOTOPE DILUTION AND SPECIATED ISOTOPE DILUTION MASS SPECTROMETRY

(75) Inventors: Howard M. Kingston, Pittsburgh, PA (US); Mizanur Rahman, Cheswick, PA (US); David Lineman, Greenville, PA (US); Mehmet Pamukcu, Sunnyvale, CA (US)

(73) Assignees: Applied Isotope Technologies, Inc., Pittsburgh, PA (US); David Lineman, Greenville, PA (US)

( * ) Notice: Subject to any disclaimer, the term of this patent is extended or adjusted under 35 U.S.C. 154(b) by 1389 days.

(21) Appl. No.: 11/952,471

(22) Filed: Dec. 7, 2007

(65) Prior Publication Data

US 2012/0142545 A1    Jun. 7, 2012

Related U.S. Application Data

(60) Provisional application No. 60/873,383, filed on Dec. 7, 2006.

(51) Int. Cl.
- *G01N 1/38* (2006.01)
- *G01N 30/72* (2006.01)
- *G01N 33/53* (2006.01)

(52) U.S. Cl. ........ 436/179; 436/173; 436/178; 435/7.92

(58) Field of Classification Search ........................ None
See application file for complete search history.

(56) References Cited

PUBLICATIONS

Monperrus et al. Simultaneaous sample preparation and species-specific isotop dilution mass spectrometry analyses of monomethylmercury and tributytin in a certified oster tissue. Anal. Chem. 2003, vol. 75, pp. 4095-4102.*

* cited by examiner

*Primary Examiner* — Shafiqul Haq
(74) *Attorney, Agent, or Firm* — Barbara E. Johnson, Esq.

(57) ABSTRACT

A method for the equilibration of enriched isotope species and natural isotope species prior to mass spectrometric analysis using solid phase and/or microwave isotope ratio equilibration and measurement.

10 Claims, 22 Drawing Sheets

Figure 1:
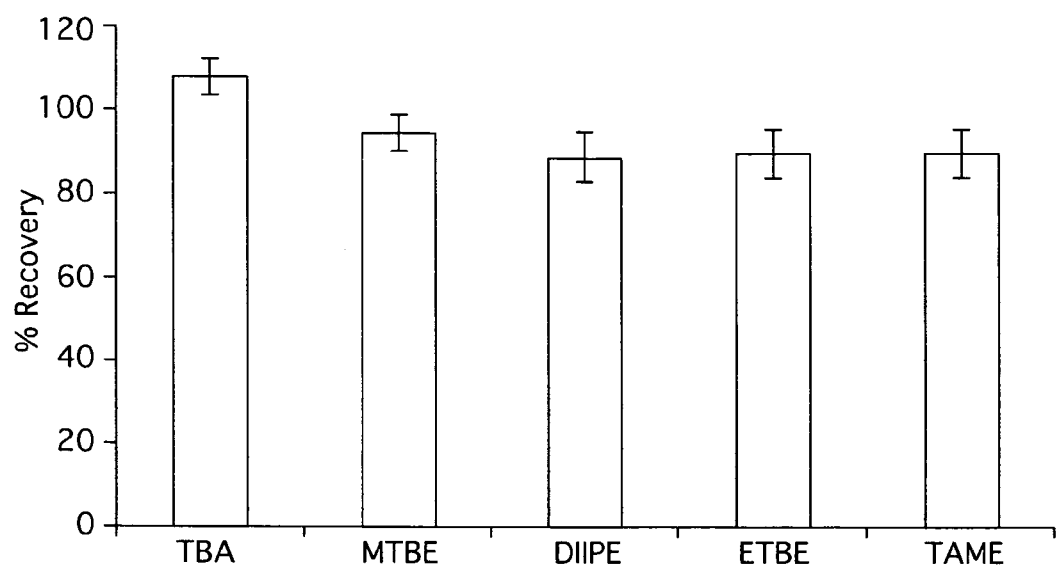

SOLID PHASE AND CATALYZED ENABLED AUTOMATED ISOTOPE DILUTION AND SPECIATED ISOTOPE DILUTION MASS SPECTROMETRY

CROSS REFERENCE TO RELATED APPLICATIONS

This application claims the benefit of U.S. Provisional Patent Application No. 60/873,383, filed Dec. 7, 2006, and entitled "Equilibration Methods Using Microwave Radiation", the contents of which are incorporated herein by reference.

BACKGROUND OF THE INVENTION

1. Field of the Invention

The present invention relates to a method of improving equilibration of enriched isotopes and tagged species and natural isotope species by using solid phase immobilization of isotopically enriched species and equilibration and simultaneous extraction, separation, and/or selection of the species of analytical interest of the isotopes of the natural and the tagged species on the solid phase and improvement of portability of IDMS and SIDMS and other methods of improving efficiency and equilibration and automation.

2. Description of Related Art

IDMS and SIDMS are based on enriched isotope equilibration with the exact species analytes to be measured. Patents describing Isotope Dilution Mass Spectrometry (IDMS) and Speciated Isotope Dilution Mass Spectrometry (SIDMS) and the use of equilibrated solutions and these patents are referenced herein—see U.S. Pat. Nos. 5,414,259 and 6,790,673 B1 and 6,974,951 B1, and 5,883,349, and 5,830,417 and 7,005,635 B2, and 7,220,383 B2, Pat. pending No. US 2002/0198230 A1 disclosing methods of preparing samples for measurement and measuring chemical species present in samples, not only its bulk chemical concentration but also on-line for automation and for improved, sensitivity, accuracy and efficiency based on these methods. The disclosure of these patents is expressly incorporated herein by reference.

SUMMARY OF THE INVENTION

A method for the catalyzed equilibration of enriched isotope species and natural isotope species prior to mass spectrometric analysis using solid phase isotope ratio equilibration and measurement is disclosed. The bases of this invention are molecular, elemental and speciated, and quantitative and qualitative sample preparation for definitive qualitative and quantitative analyses of the analytes of interest. The method improves equilibration by utilizing solid phases which have many advantages over liquid and gas phase through simultaneous equilibration and enables automation of IDMS and SIDMS analysis known in the art. The innovation uses solid phases and immobilized enriched isotope reagents, isotopically enriched molecularly manufactured reagents and the process of equilibration on solid and immobilized phases. Algorithms are used to determine mathematically concentrations and directly to correct for species shifts without calibration curves being applied to the mass spectrometric data. Time required to equilibrate and separate the analyte is significantly decreased through sample preparation on solid phases as compared to conventional liquid/thermal equilibration and separation protocols. Reagents and products made for solid phase isotope spiking and equilibration are stable over longer periods of time, thus making it possible to do on-site sample preparation and improve on storage and chain of custody problems associated with degradation of reagents and/or samples while in storage or during shipment. For field workers and laboratory analysts, solid phase isotope spiking and equilibration will make handling of reactive and toxic materials safer in field-spiked and equilibrated forms than they are as bulk reagent solutions, by eliminating several sample preparation and manipulation steps. The sample analyte and isotopically enriched and equilibrated reagent tags are either eluted off for analysis in liquid and/or gas phase or are directly analyzed in solid phase by surface ionization into the mass spectrometer. Solid phase isotope spiking and highly rapid equilibration facilitate the ability to design cost-effective, high-throughput, reliable sample preparation and analysis systems involving high levels of automation and miniaturization sub-systems, thereby making it possible to design highly portable, field-deployable, accurate, low-false positive analytical and detection systems. Such field deployable systems will be highly useful for environmental forensics, homeland security and homeland defense, industrial regulation compliance, biosciences and clinical research and clinical diagnostic purposes. Some of the homeland defense and homeland security applications include multi-point drinking water network monitoring for fugitive agents and air/water/surface analyses in the battlefield for the protection of armed forces. These systems will also be useful for assessing risks of certain diseases in humans as a function of exposure to industrial toxins from the environment and food within the growing field of environmental health. Eventually, such system may turn into tools that will help predict the onset or slow down the progression of certain diseases like autism, some forms of cancer, and immunodegenerative diseases like Alzheimer's, Parkinson's and diabetes. Definitive study using both concepts described above follows infra.

BRIEF DESCRIPTION OF THE DRAWING(S)

FIG. 1: Results from oxygenates equilibrated and separated by SPI-SPE as described and analyzed by GC-MS.

Figure 2:
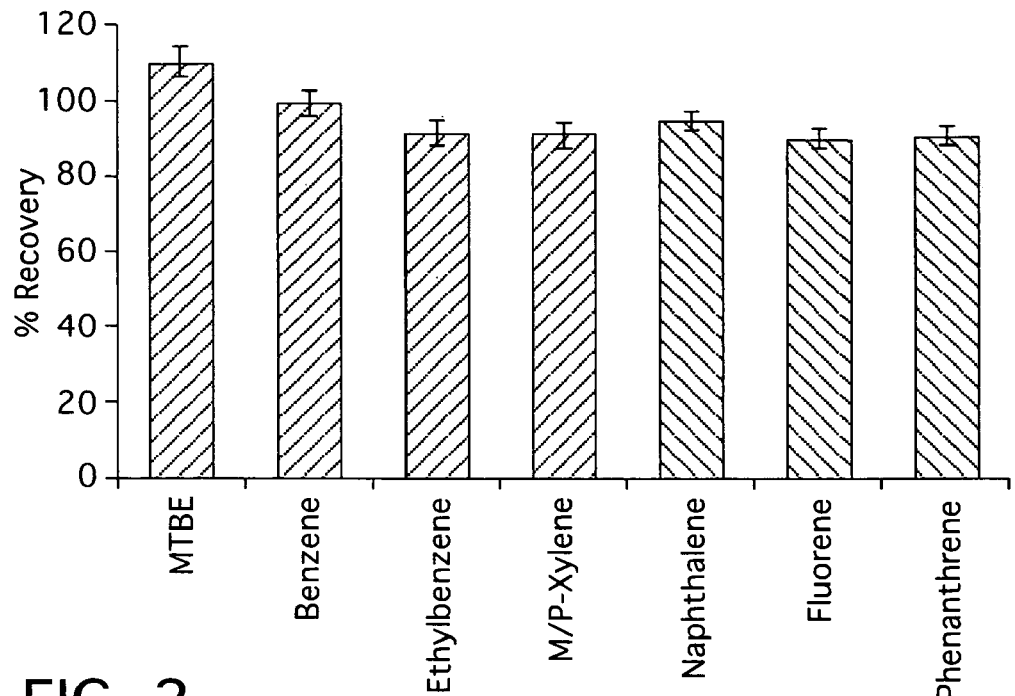

FIG. 2: Results on PAG-5 column spiked with indicated oxygenates and equilibrated and separated on the column as described and analyzed by GC-MS.

Figure 3:
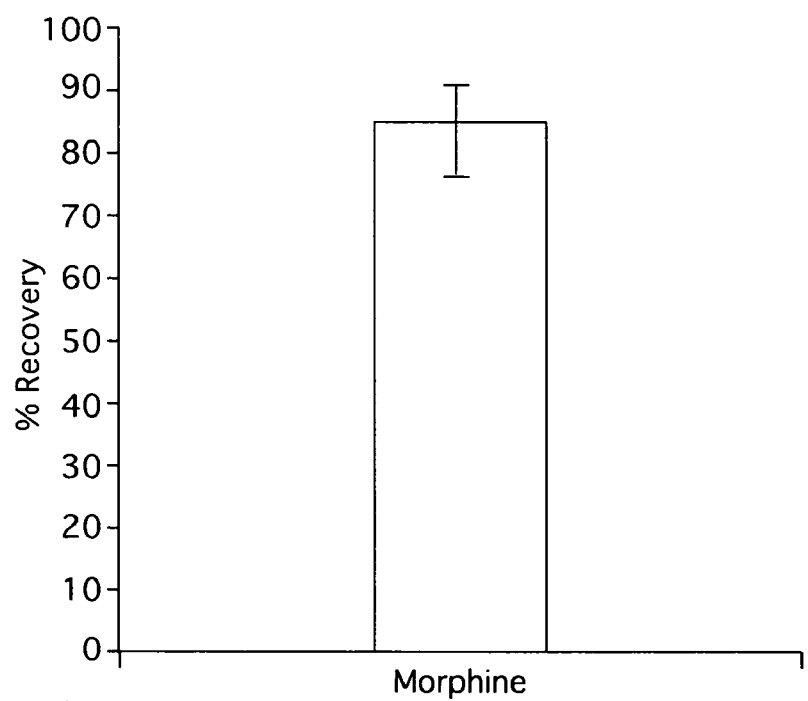

FIG. 3: Morphine from serum using Agilent Evidex, 6 ml, 0.5 g of C-13 isotopically IDMS prespiked morephine and equilibrated with sample morphine on the PSI-SPE column.

Figure 4:
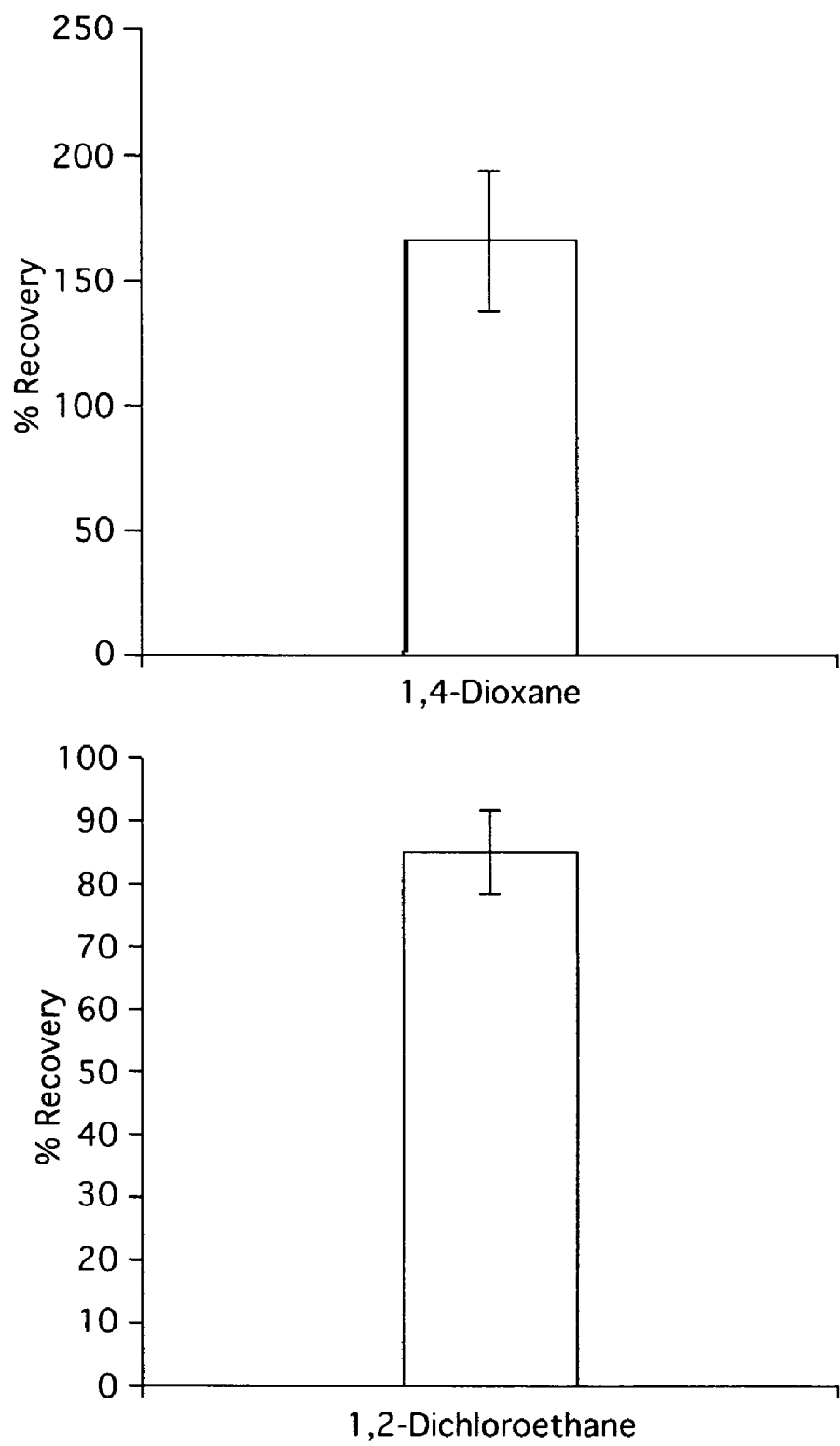

FIG. 4: 1,4-dioxane and 1,4 dichlorethane using isotopicaly enriched PSI-SPE equilibrated with the natural on the column.

Figure 5:
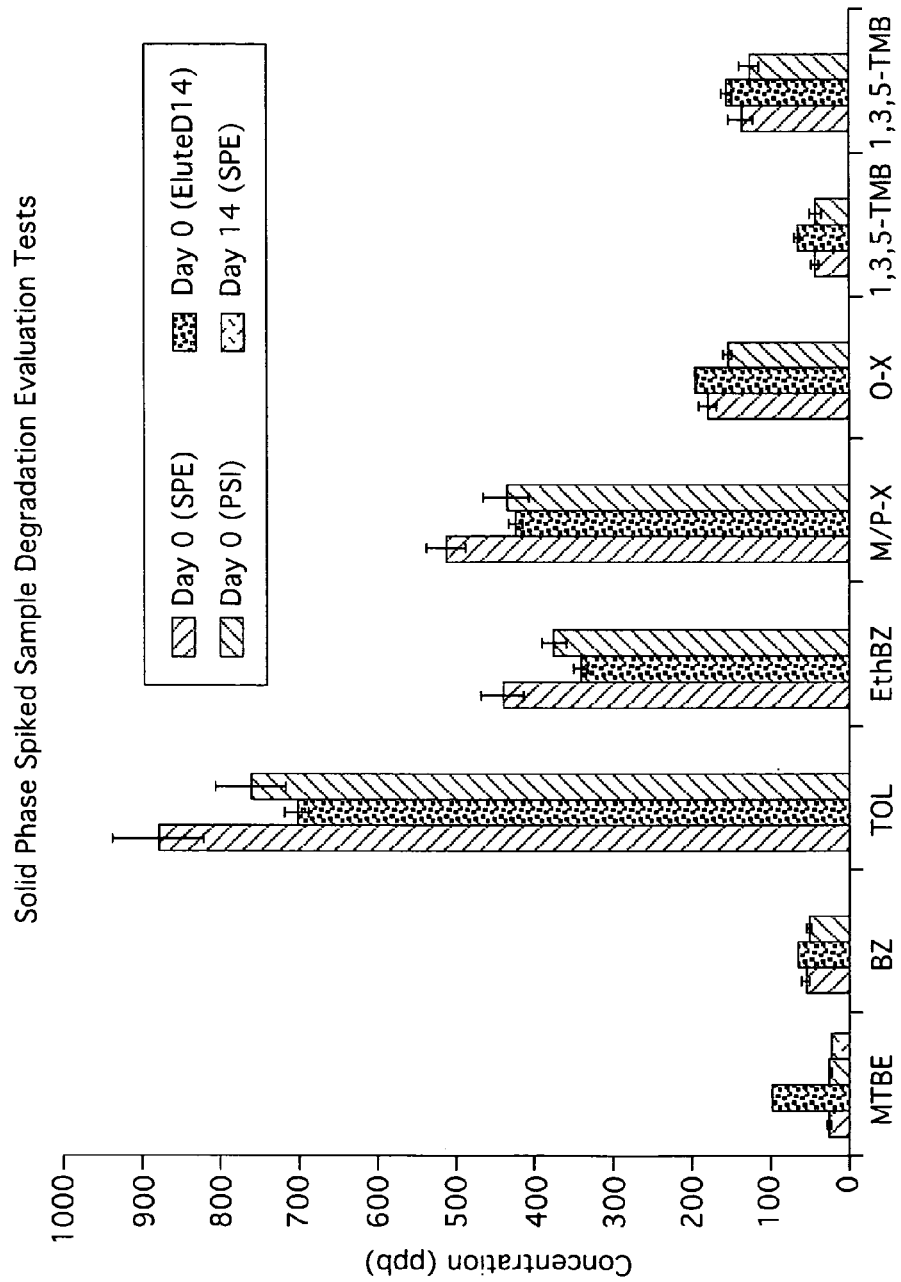

FIG. 5: Effects of biodegradation on monitoring well sample. All concentrations in ppb, Errors shown expressed as 90% CL, n=3.

Figure 6:
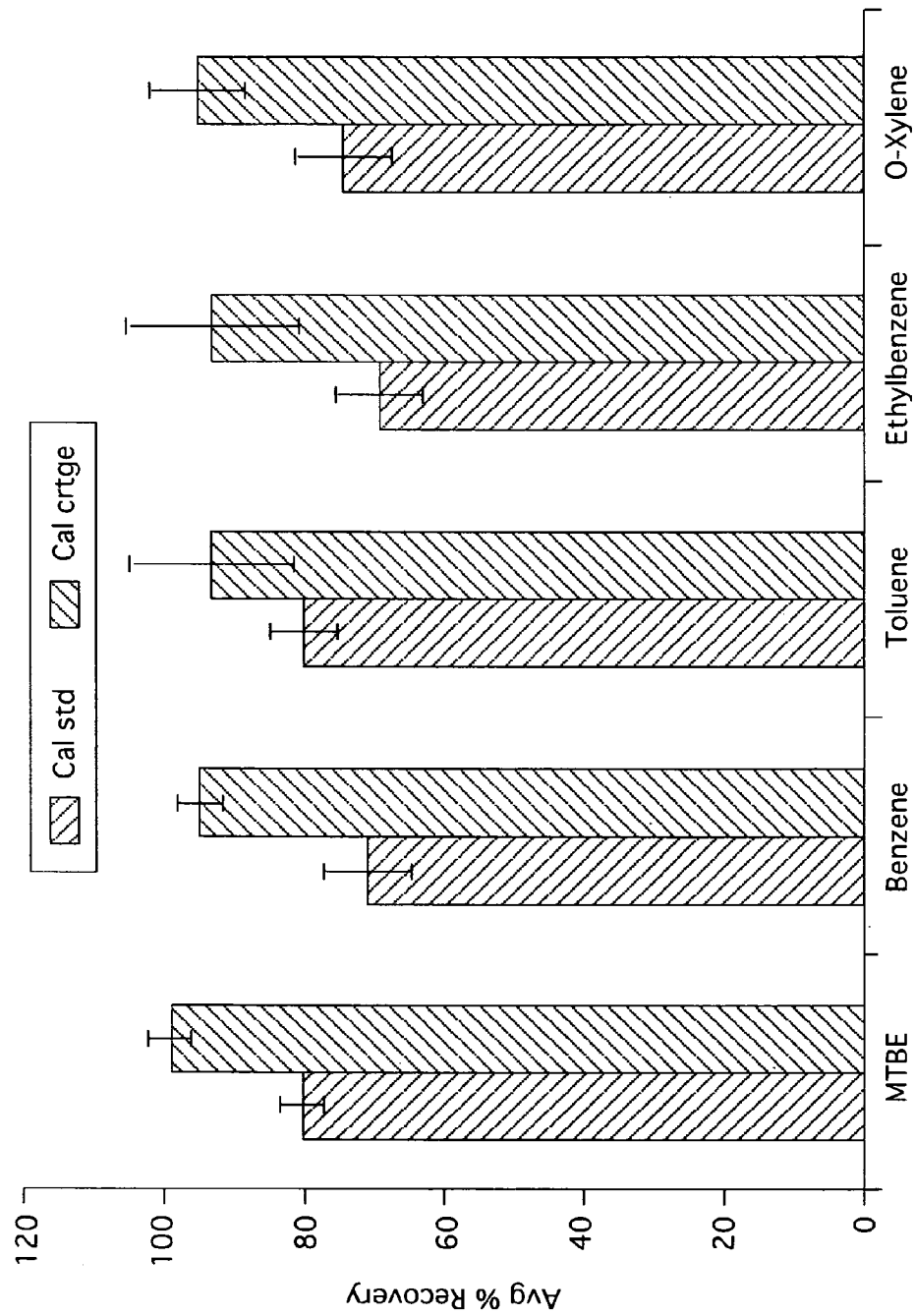

FIG. 6: Calibration Std. vs. Calibration Cartridge. Reagent water spiked at 2 ppm, Error expressed as 95% CL, n=4.

Figure 7:
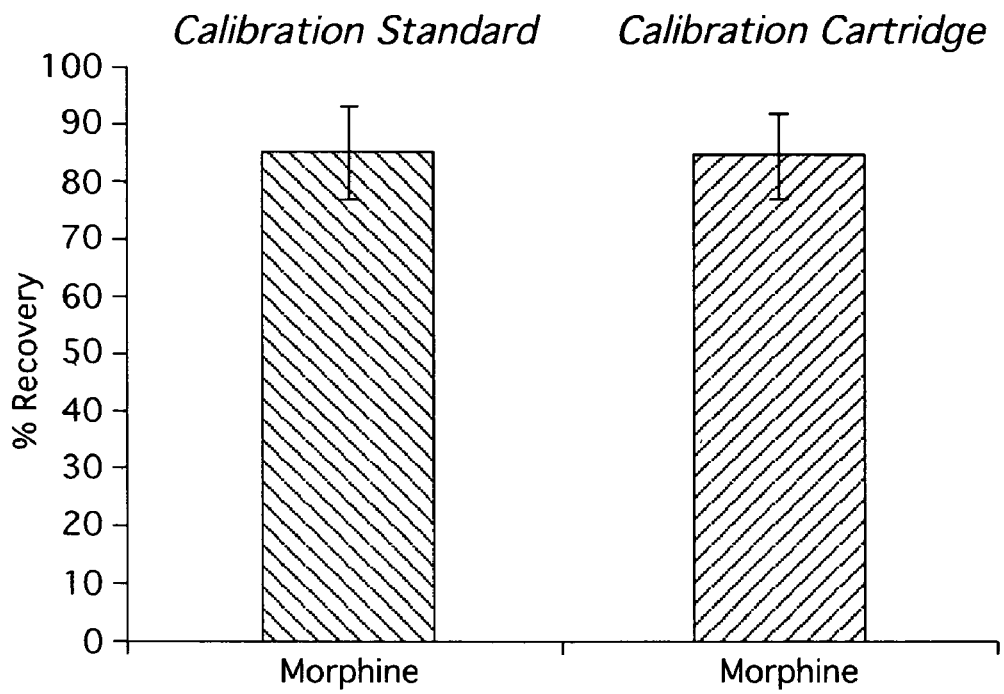

FIG. 7: Calibration Std. vs. Calibration cartridge.

Figure 8:
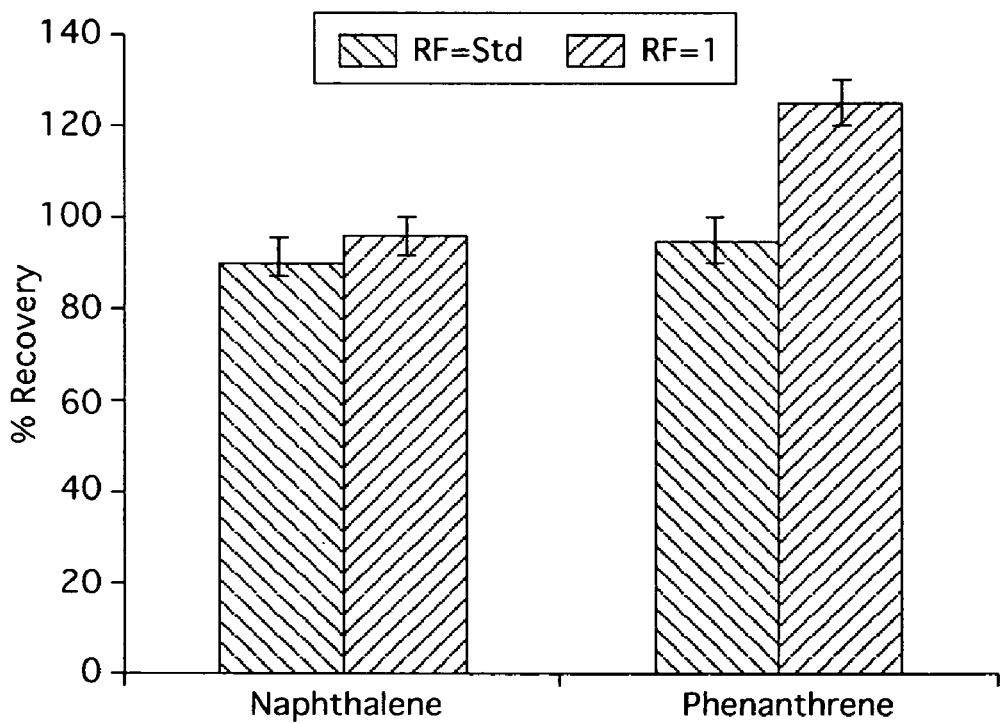

FIG. 8: RF Comparison. Calibration RF vs. RF=1.

Figure 9:
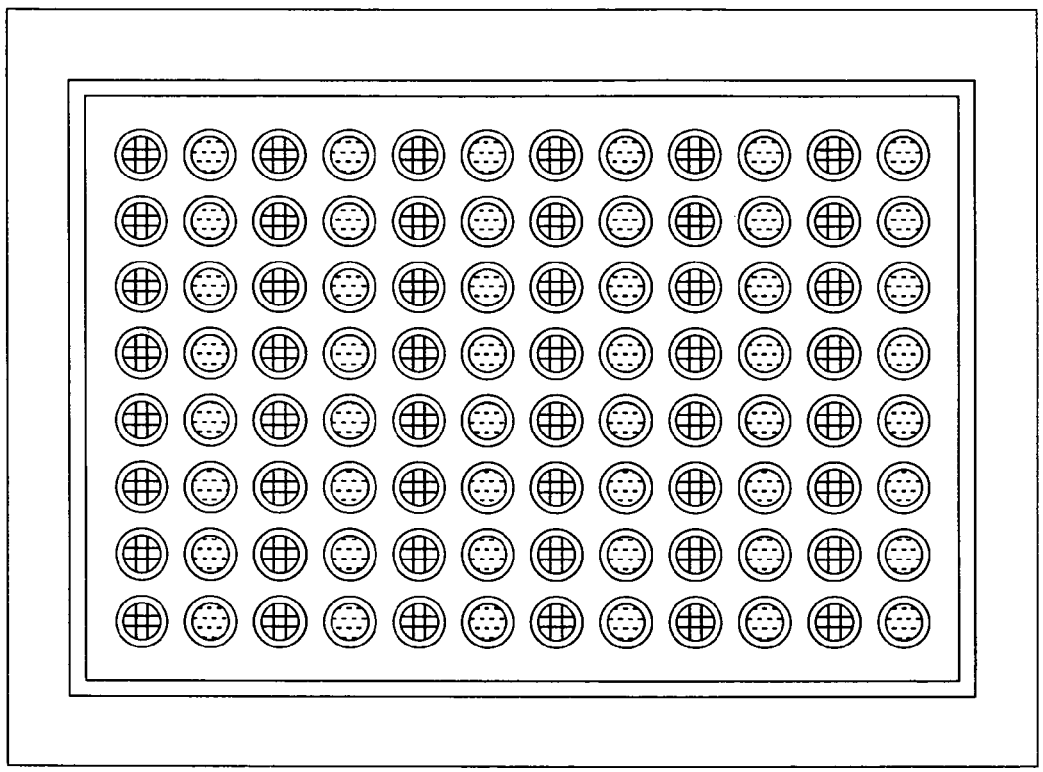

FIG. 9: Microtiter plate (top view), 8×12 (96 wells) format prepared mass spectrometric (IDMS and/or SIDMS) ELISA, with alternating rows of two different kinds of enriched isotopically modified bound antigens.

Figure 10:
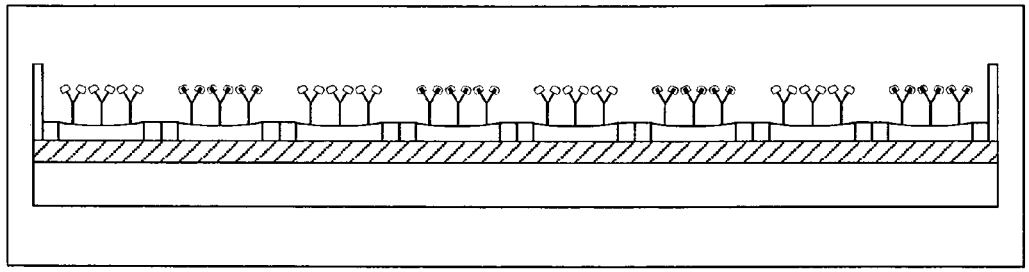

FIG. 10: Microtiter plate or a surface modified solid phase support (side view), with alternating, discrete rows of two different kinds of enriched isotopically bound antigens. One of isotopically enriched antigen is prepared as a part of the solid surface prior to implementing ELISA with the natural isotopic sample. Alternatively, no isotopically pre-loaded antigens would be present on the solid phase and both enriched and non-enriched antigens are equilibrated when bound to the antibodies, rapidly during the ELISA.

Figure 11:
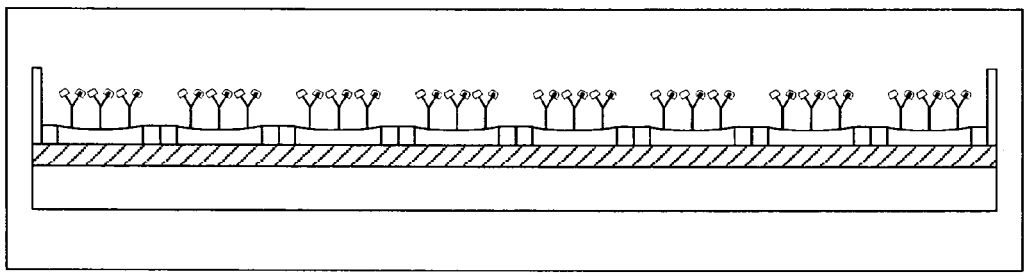

FIG. 11: Microtiter plate or a surface modified solid phase support (side view), with some percentage of the antibodies having previously bound isotopically enriched antigen. The ELISA measurement is accomplished by measuring the level of binding of the isotopically enriched antigen present in the sample as a function of ratio between these two sets of antigens.

Figure 12:
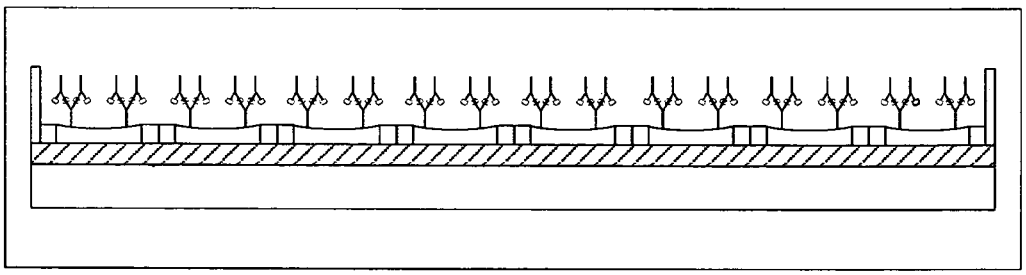

FIG. 12: Microtiter plate or a surface modified solid phase support (side view), using the sandwich system, and dual antibody and antigen analysis using isotopically enriched antigens and measuring the ratios of the two enriched isotope spikes.

Figure 13:
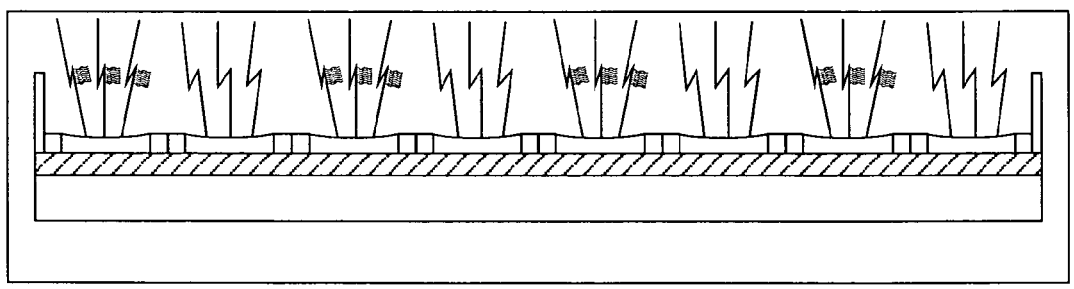

FIG. 13: Microtiter plate or a surface modified SELDI plate with natural abundance biomarkers and isotopically enriched biomarkers (side view), arranged in two discrete rows.

Figure 14:
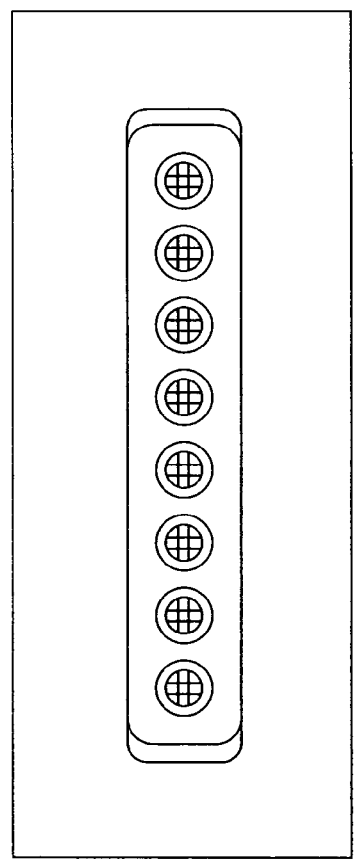

FIG. 14: Top view of an 8-well strip used for SELDI or ELISA.

Figure 15:
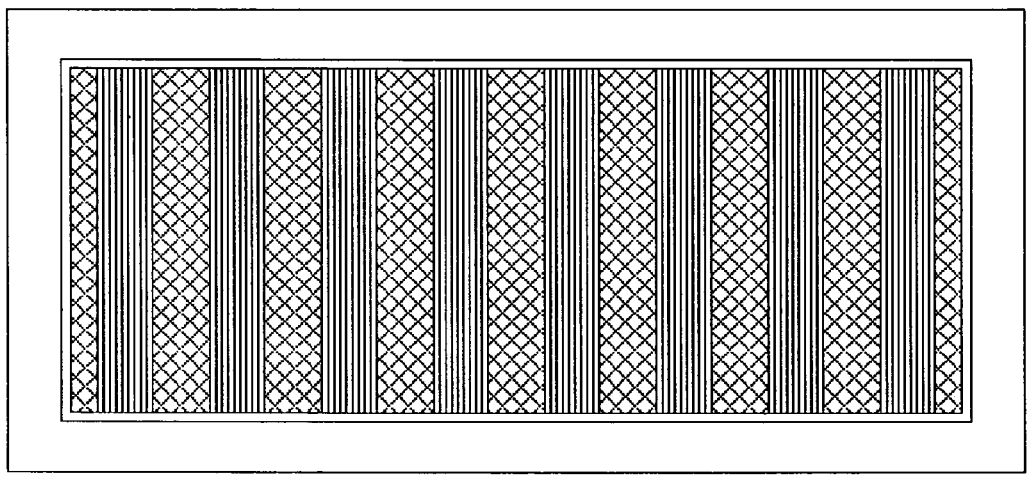

FIG. 15: A solid phase surface modified plate with 16 rows of alternating bound protein biomarkers or nucleotide probes, both enriched and natural, arranged in high density micorarray format. The quantitation is done using multi-variant biormarkers or nucleotides, both isotopically enriched and natural, and applying the IDMS and/or SIDMS direct ratio algorithms.

Figure 16:
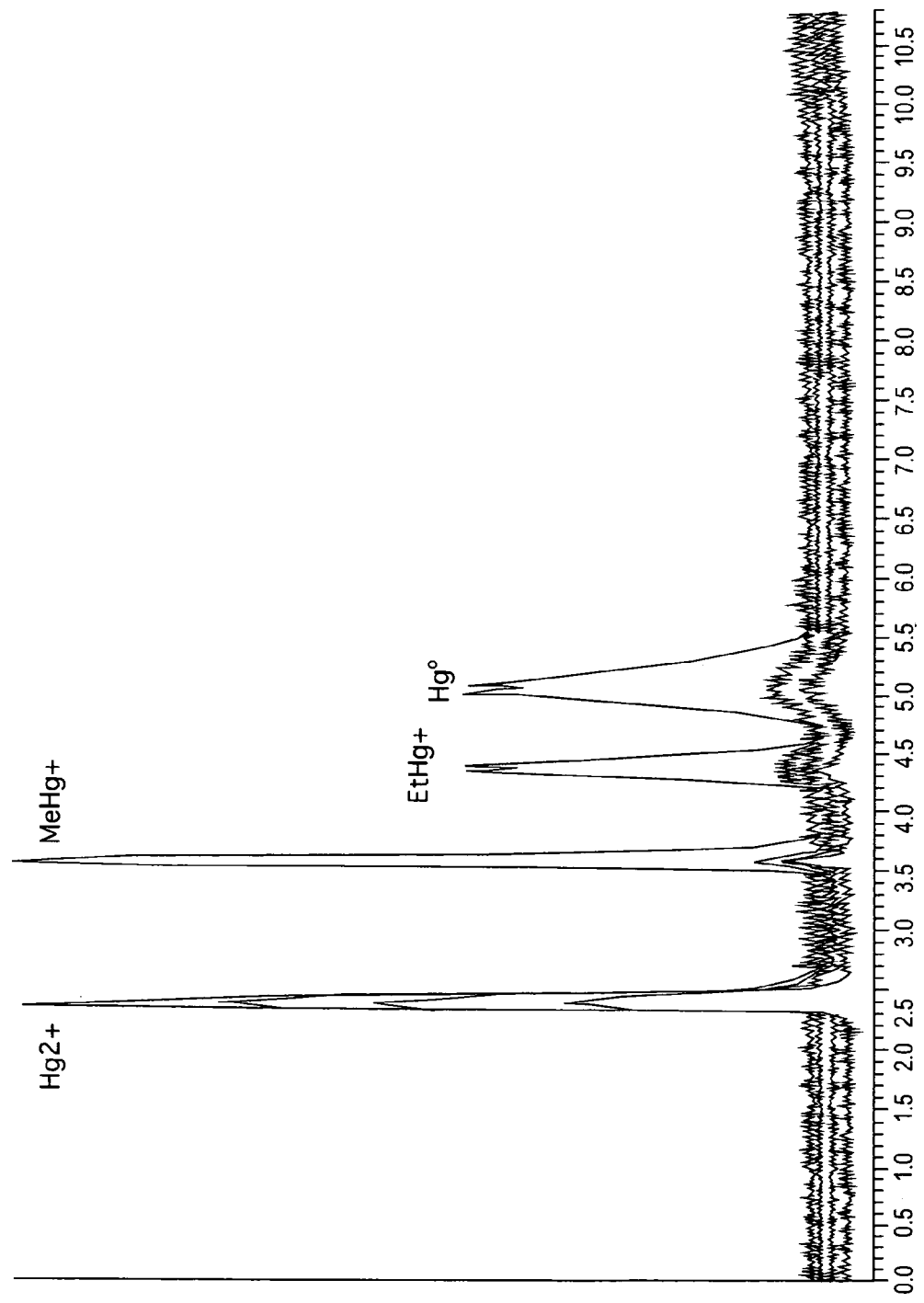

FIG. 16: Mass spectroscopy readout demonstrates the isotope enriched specific species spiking of blood for methylmercury, ethylmercury, inorganic mercury and metallic mercury.

Figure 17:
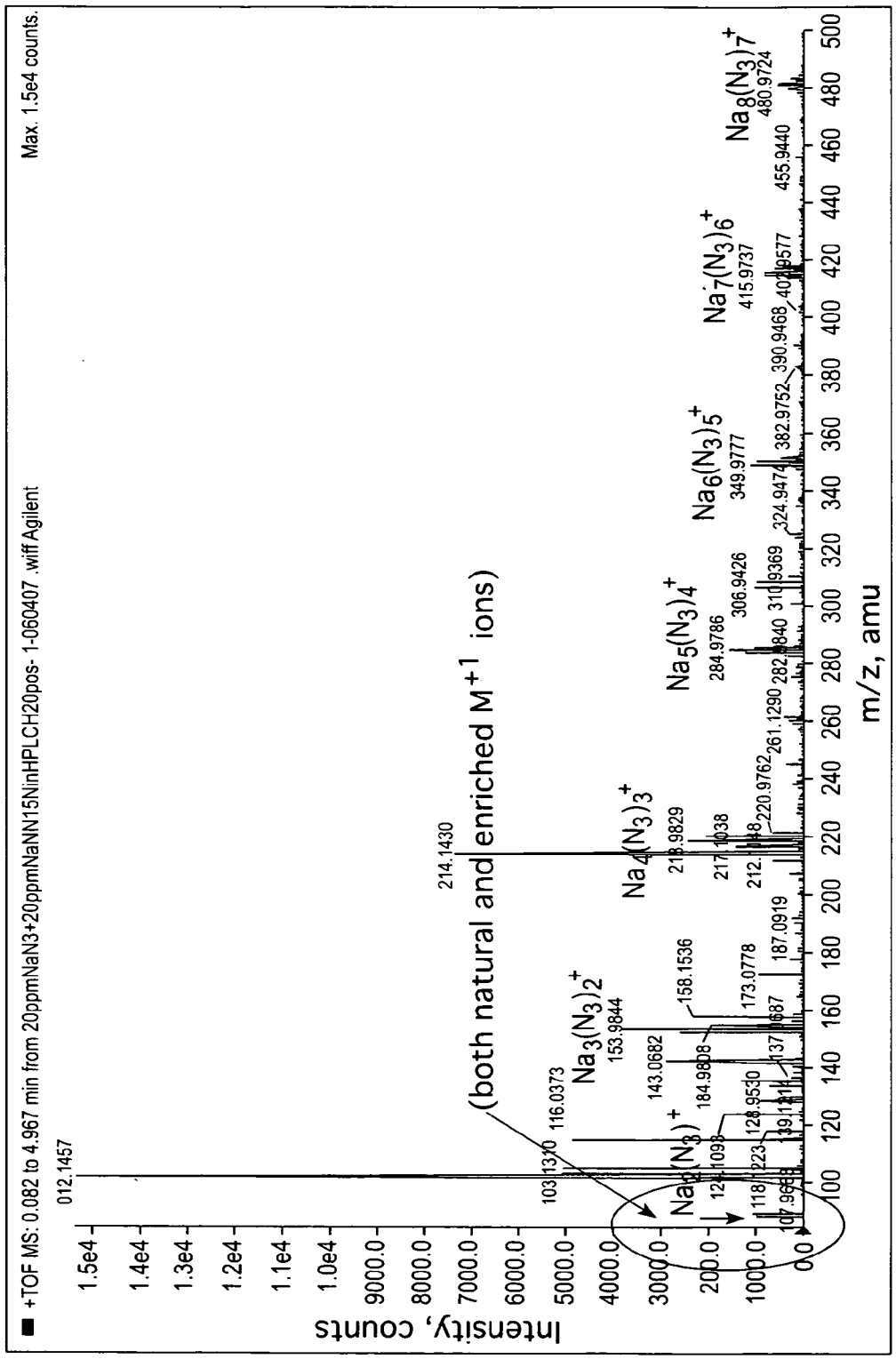

FIG. 17: Mass spectroscopy readout shows water containing 20 ppm NaN3 and 20 ppm NaNN15N by ESI-TOF-MS in positive mode.

Figure 18:
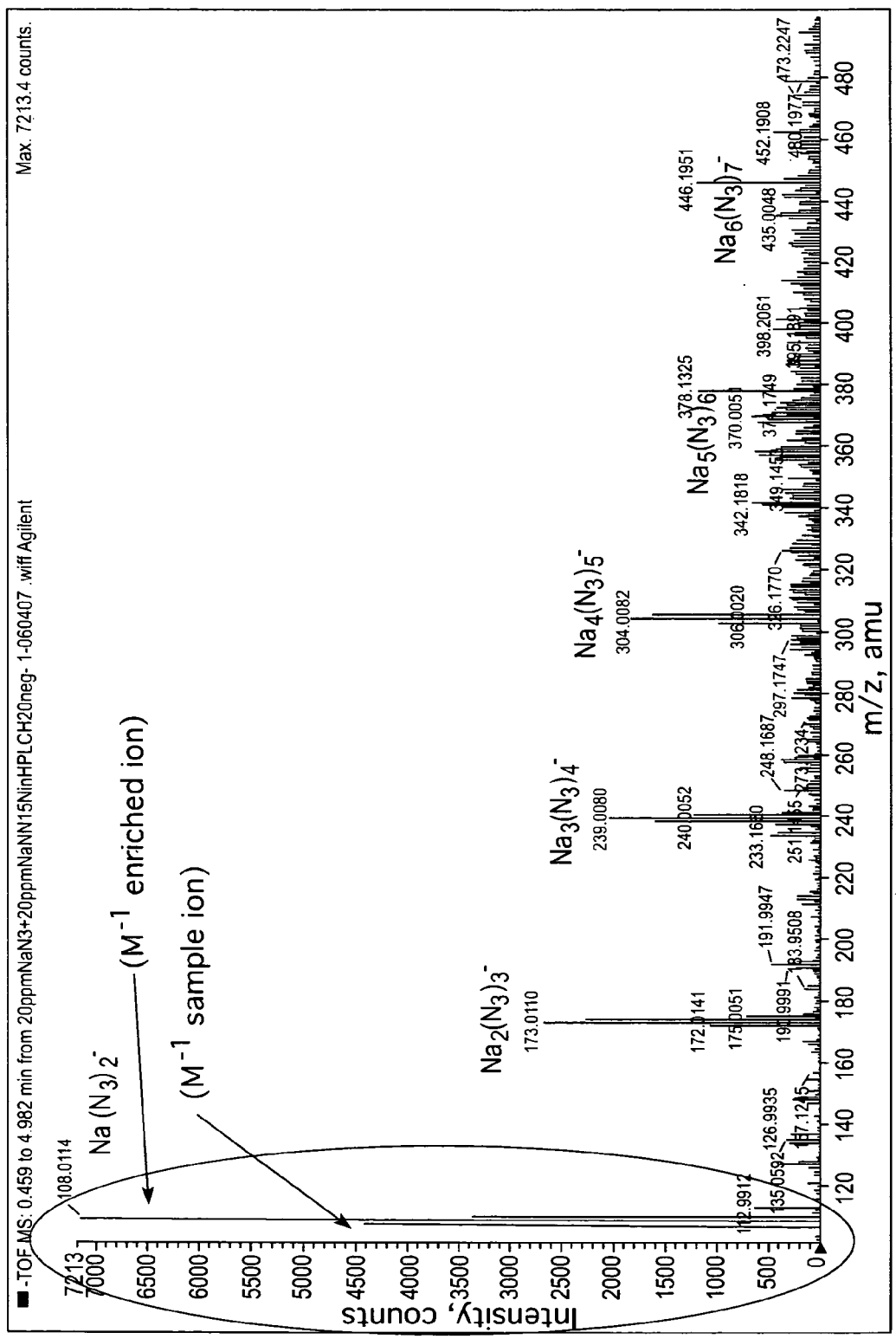

FIG. 18: Mass spectroscopy readout shows water sample containing 20 ppm NaN3 and 20 ppm NaNN15N by ESI-TOF-MS in negative mode.

Figure 19:
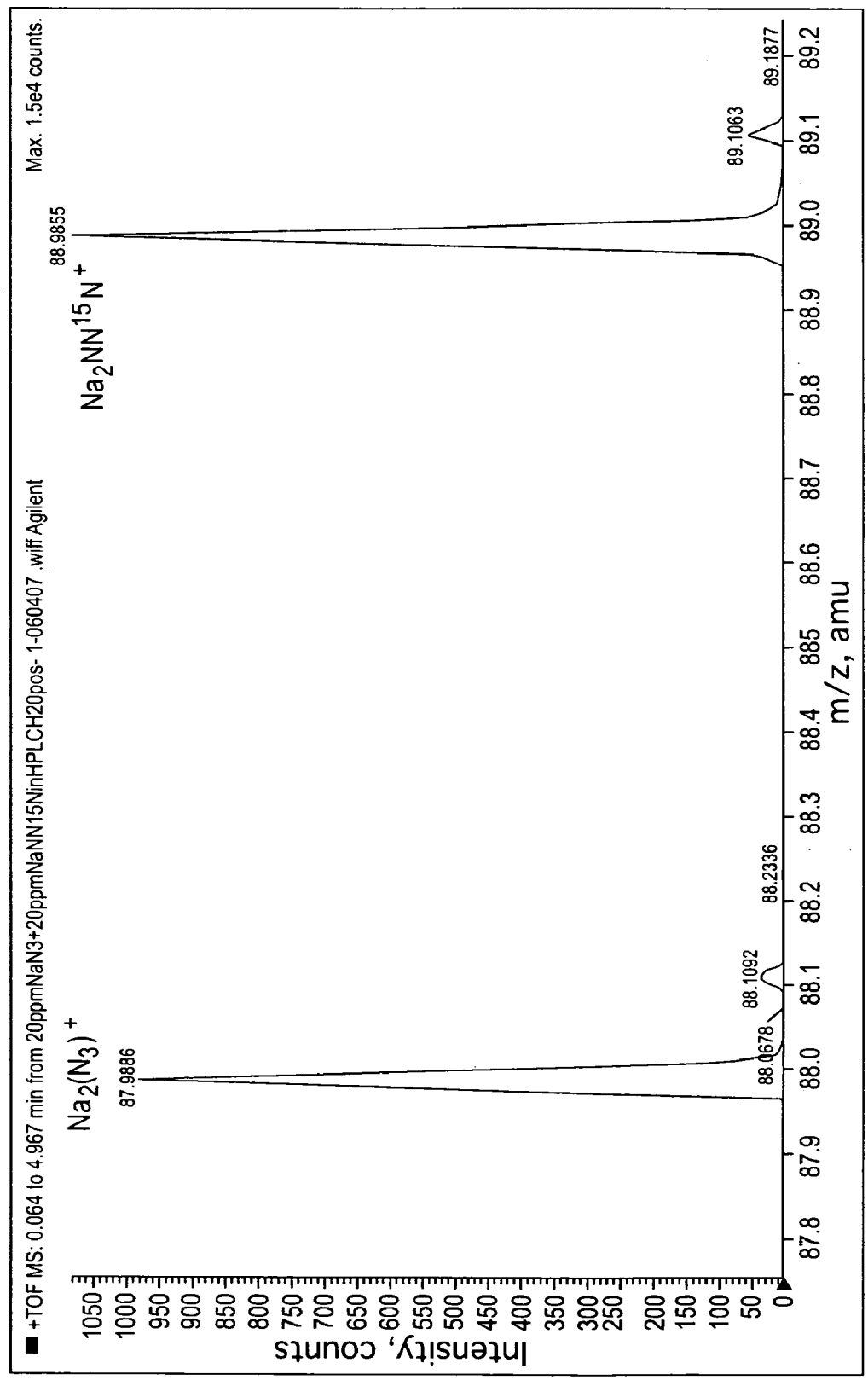

FIG. 19: Mass spectroscopy close up of one of the sodium azide ion of 20 ppm NaN3 spiked with 20 ppm NaNN15N in positive ion mode, all natural peak is at m/z 88 and all isotope peak is at m/z 89.

Figure 20:
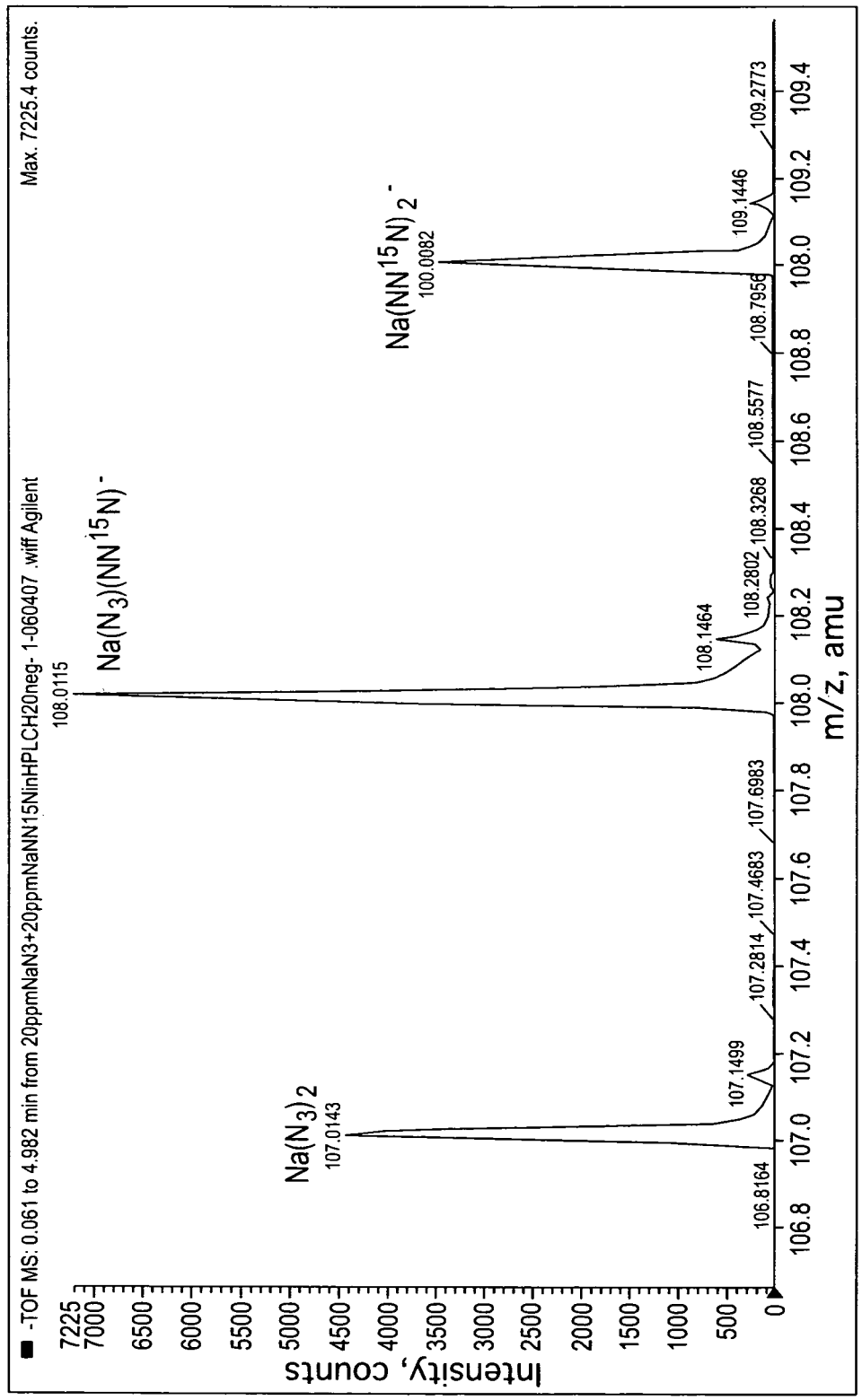

FIG. 20: Mass spectroscopy close up of first sodium azide ion of 20 ppm NaN3 spiked with 20 ppm NaNN15N in negative mode in negative mode, the all natural peak is at 107, the mixed peak is at 108 and the all isotope peak is at 109 and has a 1:2 or 1:3 ratio for quantification.

Figure 21:
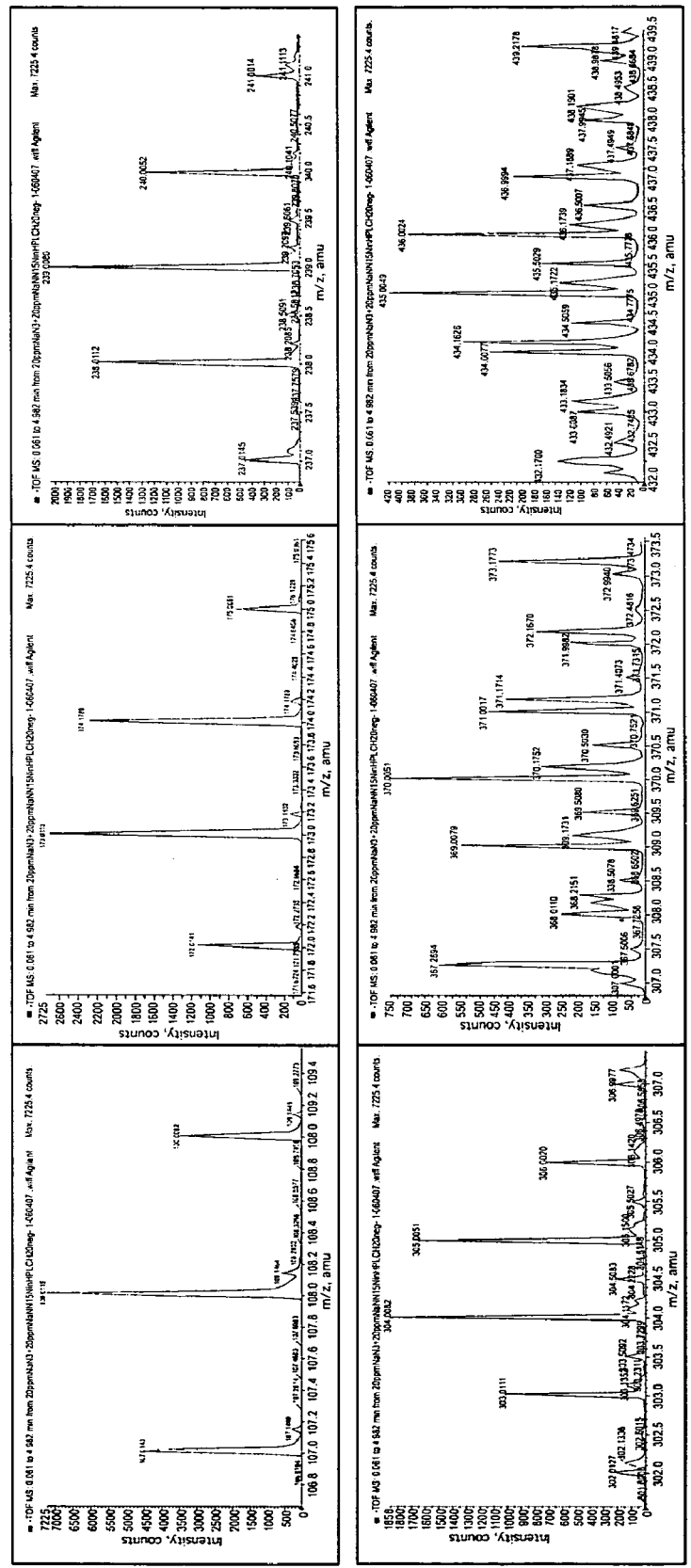

FIG. 21: Mass spectroscopy readout shows the many simultaneous ratios that are expressed in this set of molecular species and quantification requires multiple equations and multiple ratios for quantification. These collected graphics are of 20 ppm NaN3 and 20 ppm NaNN15N in DI H2O in negative mode. Each graph has one more azide peak.

Figure 22:
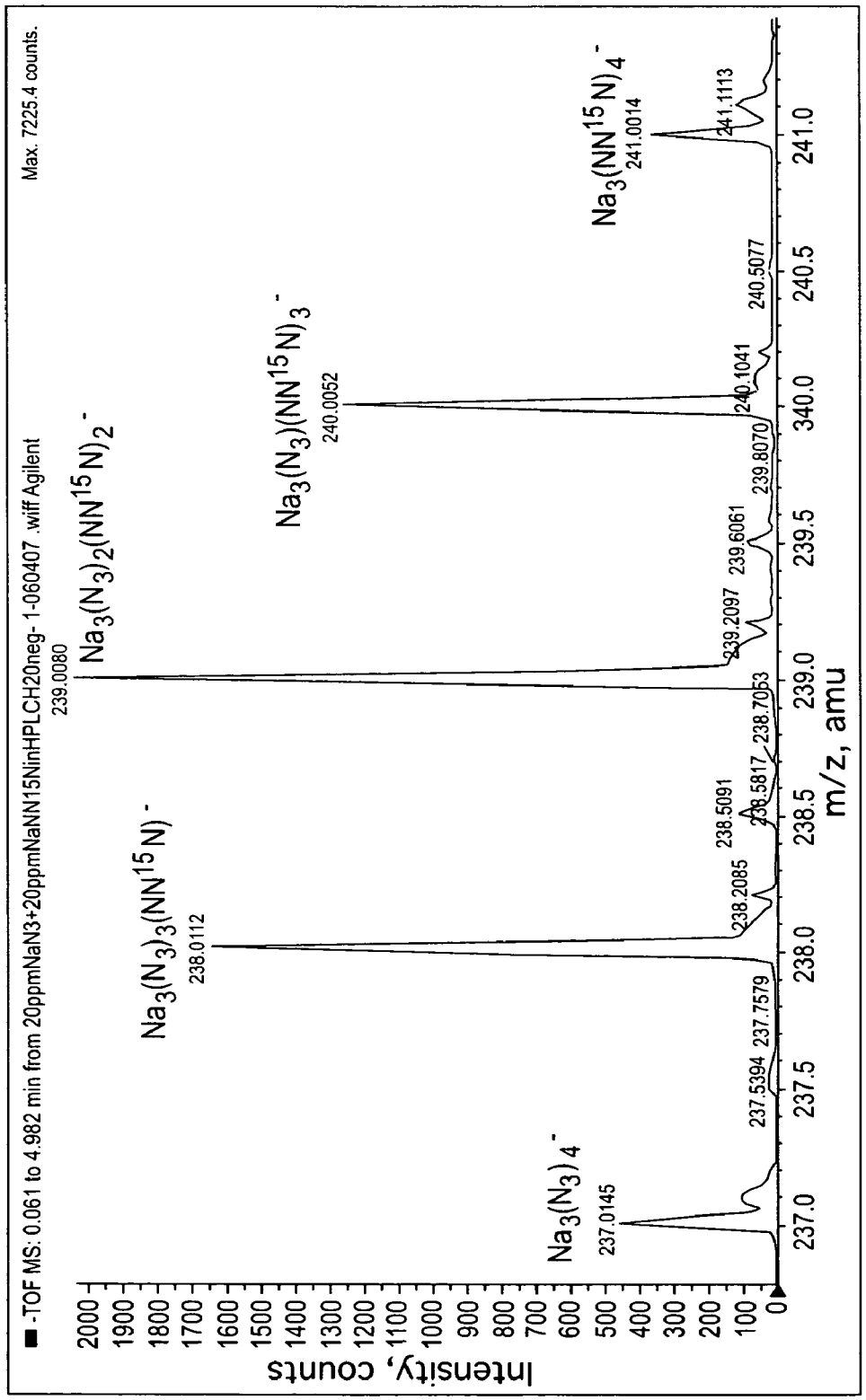

FIG. 22: Mass spectroscopy readout shows a new ratio relationship and multiple peaks between natural Azide Na3(N3)4- (left most peak) and three corresponding isotopic enriched tagged analogue of Azide Na3(N3)4- with varying numbers of N15 isotopes and ratios. This figure is the close up of third sodium azide ion of 20 ppm NaN3 spiked with 20 ppm NaNN15N in negative mode, the all natural peak is at 237, the mixed peaks are at 238, 239 and 240 and the (2×15N) isotope peak is at 241.

Figure 23:
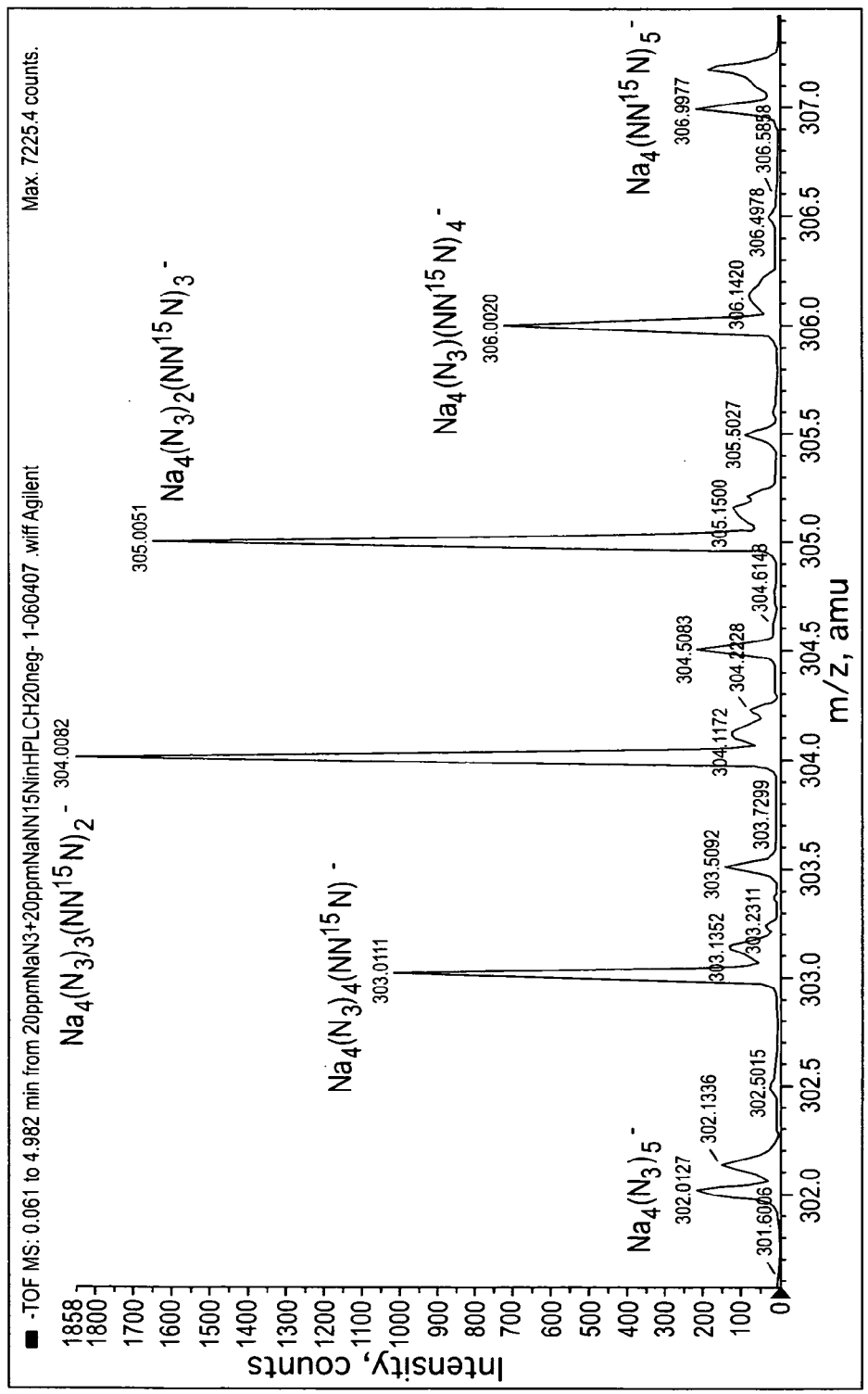

FIG. 23: Mass spectroscopy close up of fourth sodium azide ion of 20 ppm NaN3 spiked with 20 ppm NaNN15N in negative mode, the all natural peak is at 302, the mixed peaks are at 303, 304, 305 and 306 and the all isotope peak is at 307.

Figure 24:
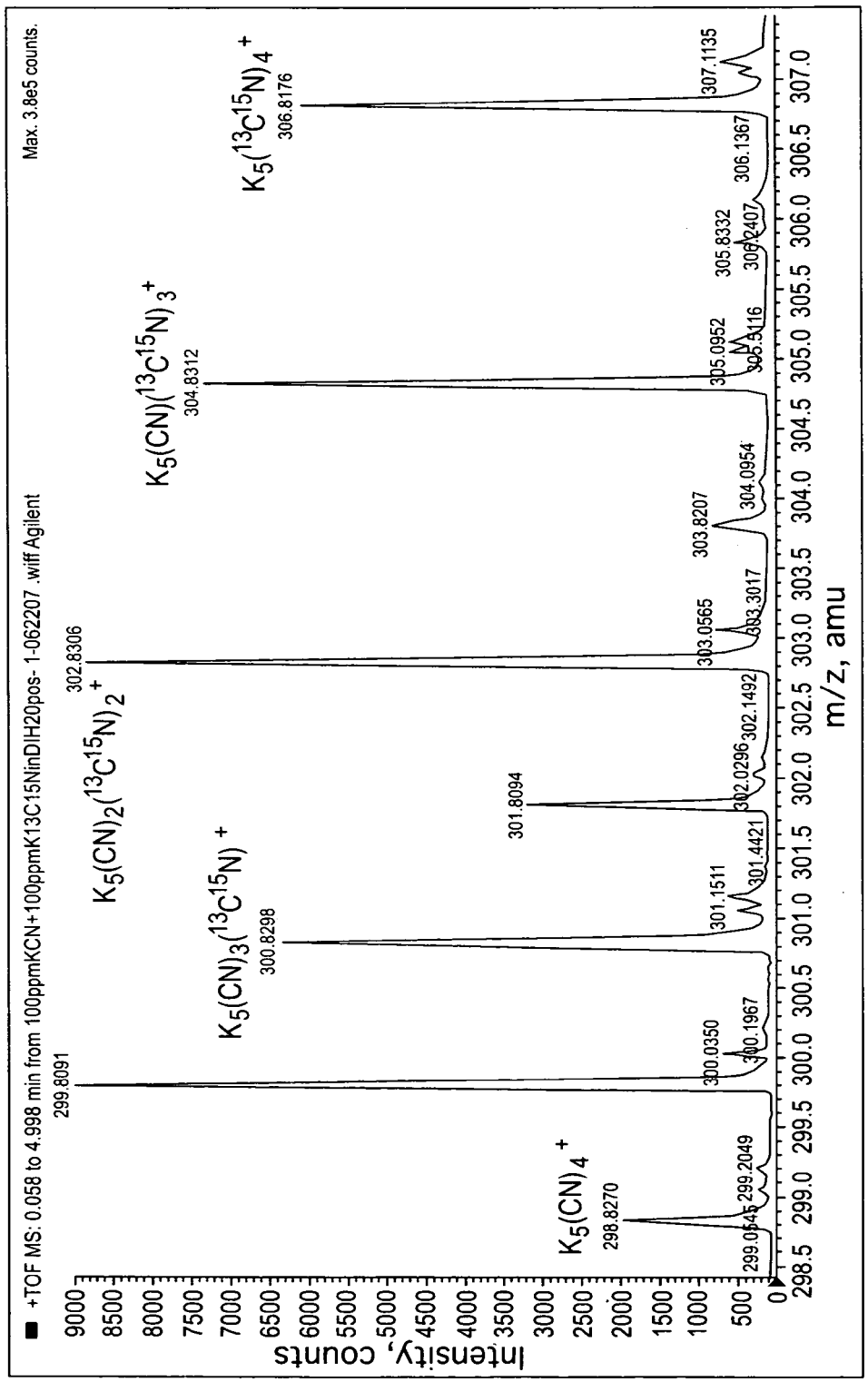

FIG. 24: Mass spectroscopy readout enhanced view of nanoESI-TOF-MS of fourth potassium cyanide species ion of 100 ppm (ug/g) KCN spiked with 100 ppm $K^{13}C^{15}N$ in positive mode, the all natural peak is at 299, the isotopic enriched potassium cyanide peaks are the peaks at 301, 303 and 305 and the all isotope peak is at 307, each has been annotated with its mix of isotopic and natural carbon and nitrogen.

Figure 25:
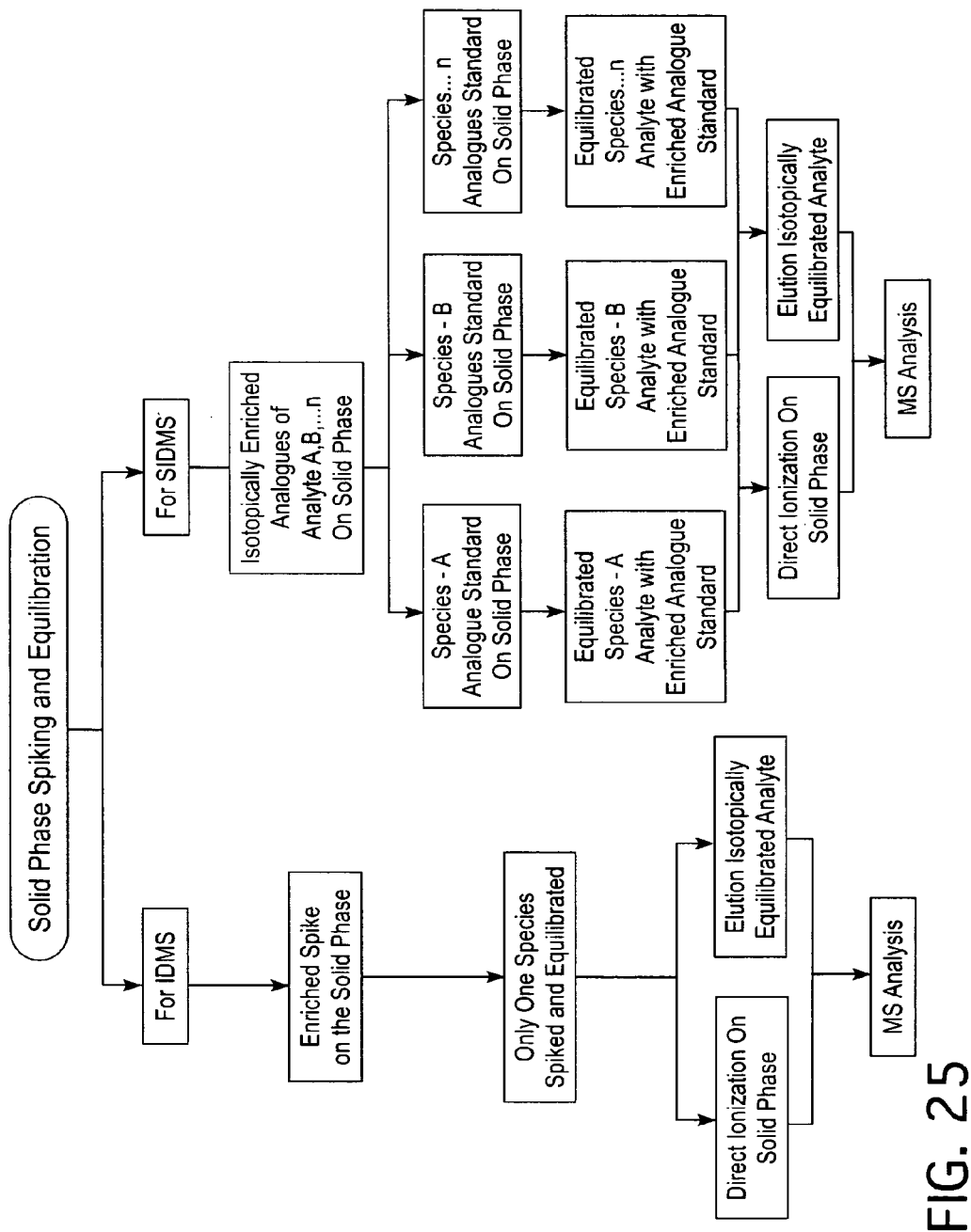

FIG. 25: Flow chart showing solid phase spiking and equilibrium.

Figure 26:
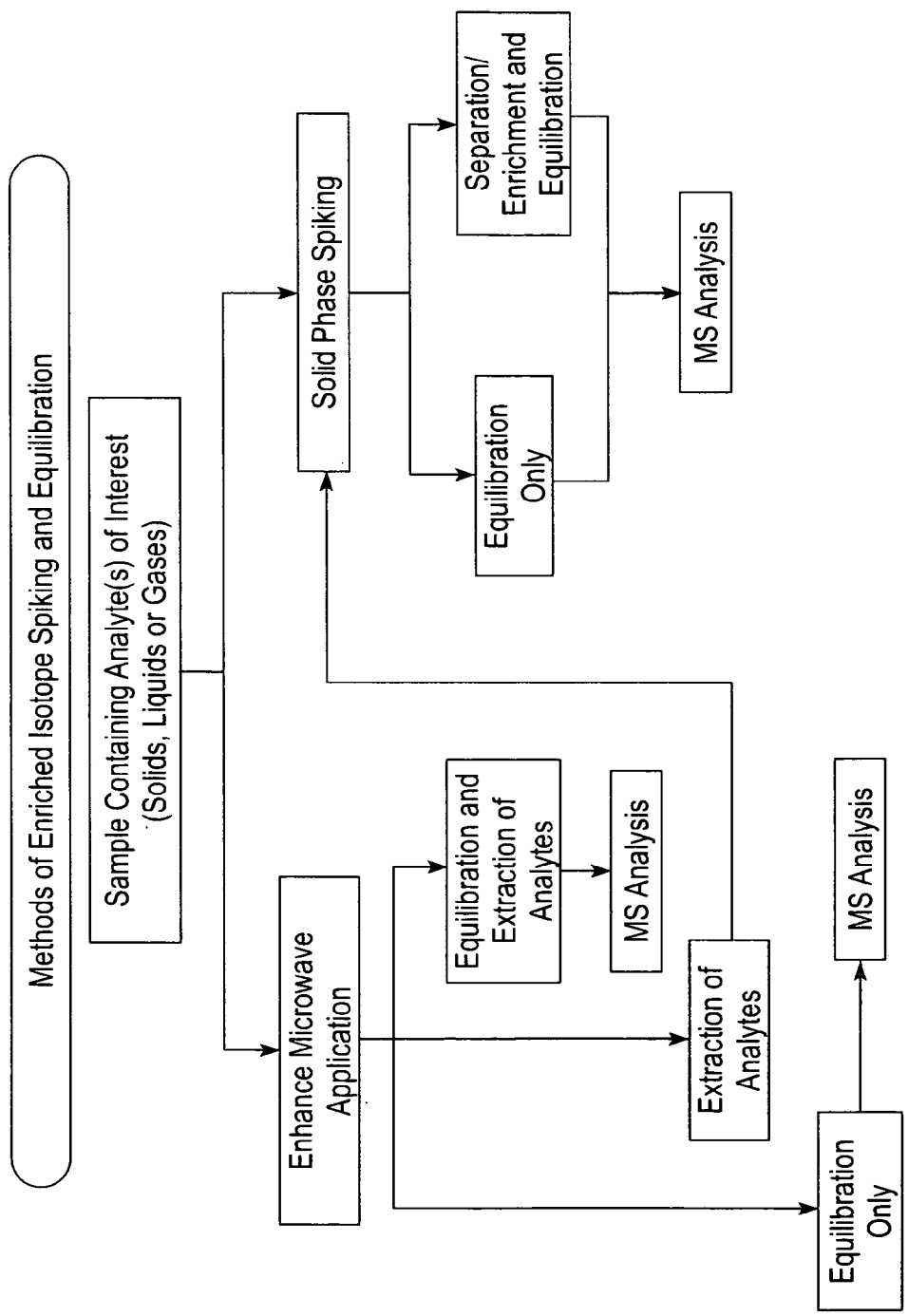

FIG. 26: Flow chart showing methods of enriched isotope spiking and equilibration.

Figure 27:
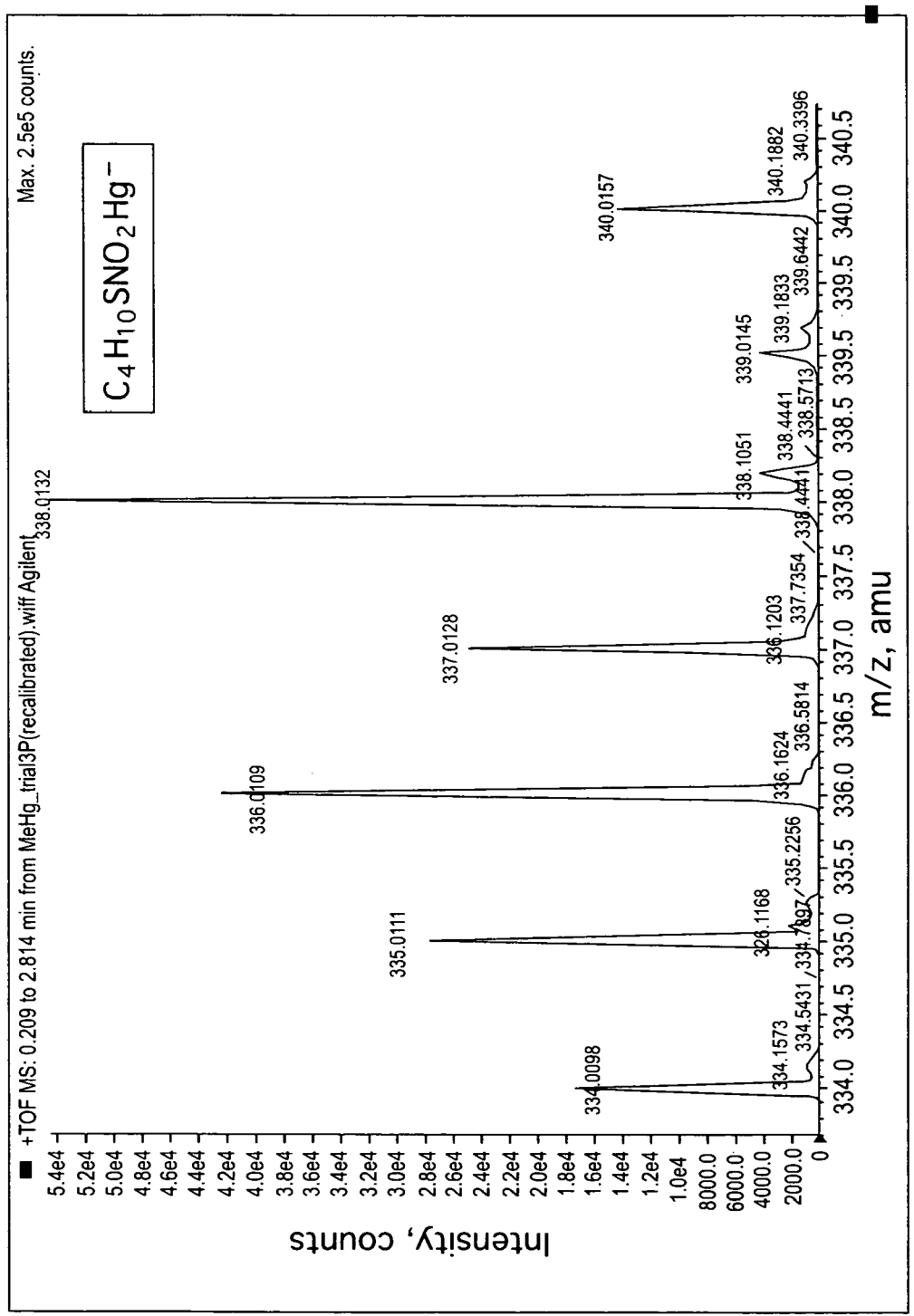

FIG. 27: Isotopic theoretical overlay and measured spectrum of methylmercury using ESI-TOF-MS at m/z 338 (Methylmercury and cysteine by ESI-TOF)

DESCRIPTION OF THE PREFERRED EMBODIMENT(S)

As used herein, "species" as employed in respect of the sample containing the species which is to be analyzed quantitatively, shall refer to any chemical species, ionic species, molecular species, complex species such as organic species, organometallic species and complex species such as metal containing proteins and hetero and homogeneous carbon species and other species which are adapted to chemical qualitative and quantitative speciated analysis of the present invention.

Problem and Solution Discussion:

Currently, sample preparation must precede measurement. To use any form of IDMS and/or SIDMS (which includes species specific isotope dilution mass spectrometry—SSIDMS), it is required that equilibration of the enriched isotope species with the natural isotopes of the species analyte be achieved first. If the time for this step takes days or hours and the instrumental analysis and automation time takes only seconds, then there is a time differential preventing use of IDMS and/or SIDMS in an automated manner. If the sample has to be extracted, separated or manipulated, an automatable method that speeds up equilibration while also performing the extraction and/or separation is necessary. Such a method has not yet been identified specifically for efficiency optimization, reproducibility and time savings resulting from accelerated equilibration and automation of IDMS/SIDMS. The invention herein addresses this problem, and results in stability and safety of handling toxins which are particularly important for applications in the fields of Homeland Defense and Homeland Security, Environmental and Environmental Forensics, Life Sciences and Industrial Regulation Compliance measurements.

Equilibration of natural and stable enriched isotopic species analogues (and radioactive ones for that matter) is required for the use of Isotope Dilution (ID) and Speciated Isotope Dilution (SID) to establish the isotopic ratio measured by a mass spectrometer. The use of ID and SID permits direct qualitative and quantitative mass spectrometry that produces an exceptionally accurate analytical quantitative analyses of the species of analytical interest. Thus equilibration of precise and unaltered isotopically enriched species and that of the natural isotopic species is absolutely essential prior to the application of the ID and SID methods by the mass spectrometer. Currently practiced equilibration may take hours or days using standard thermal methods. Some examples of these older methods are provided, later in this document. The enriched isotope solution may be so dilute that it is not stable or multiple species in the solution may interact with the enriched isotope before use. The enriched isotopes may not be safe to ship in concentrations that are stable. Prior to this invention, the IDMS and SIDMS methods remained a tool only for those with high education, skills and experience. The inexperienced and unskilled may not know how properly to extract the species, then spike, equilibrate in order to obtain quantitation. The shipping, storage, handling, field use, laboratory use, quantitative transfer, equilibration with the sample, extraction of analyte, separation of analyte or matrix, and calculations of concentrations of the analytes have been problematic for the inexperienced analysts. This invention describes methods of improving the stability of the enriched isotope spikes, the spiked species of analytical interest, ease of use, reliability of critical procedures, including equilibration and automation, thereby making the practice and use of IDMS and SIDMS possible for general use by minimum skill personnel and address high-throughput needs of commercial laboratories that often need fast, reliable analyses of large numbers of samples.

The use of solid phase sorbants to separate analyte from matrix has been known since modern chromatography was developed in the mid $19^{th}$ century. However, the use of solid phase sorbants to equilibrate the enriched stable isotopic species and to separate matrix and analytes thereby enhancing the applicability and usability of IDMS and SIDMS, as disclosed here, has not been done. In this invention, solid phase material with various different properties are used to hold the enriched isotope species and then deliver them for sample preparation, sample storage or safety purposes, to a laboratory or field-site so that the spike is already in the solid phase and not in reagent solution needing manipulation. The same solid phase used for holding the enriched isotope species can also be used to extract the analyte species.

Solid phases for use herein are selected from the group of ion exchange, adsorption medium, solid phase extraction resins, resin bonded solid phase, surface-modified filters, dual-state liquids used in immobilized liquid extraction (ILE) and fibers such as solid phase microextraction (SPME). The isotope enriched molecular or ionic species are stabilized or captured or held, chemically or physically, on the solid phase, chromatography or extraction material. The sample containing the species of analytical interest is then added with the natural sample material species of interest and is retained by the appropriate mechanism of this media used to hold the species on the media. This process can be reversed with both species, enriched and natural, eluted in equilibrated relationship. The outcome is that the species will become equilibrated and when the species of interest is eluted from the stationary phase or solid phase extraction or chromatography medium the sample mixture is a combination of equilibrated isotopic enriched and natural isotopic material ready for ID and SID mass spectrometry. In these cases, the ionization methods would be specific for a solution or gas phase such as electrospray ionization (ESI) or nano-ESI, or atmospheric pressure chemical ionization (APCI) or electron impact (EI) or inductively coupled plasma (ICP) or microwave induced plasma (MIP) and other ionization methods. This invention speeds up equilibration in the eluted liquid solution by removing the matrix that may prolong or inhibit or prevent equilibration and placing it on both analytes on the solid phase medium that produces an equilibrated state for elution simultaneously as both species having the same chemistry and affinity being the same molecules but with different isotopic ratios. One embodiment permits field or close-proximity use as even for small quantities and concentrations which otherwise would be too dilute to be shipped or be unstable without the solid phase support material. Another embodiment enables the sample species now equilibrated on the solid phase to be shipped or transported to the analysis site as enriched isotope and natural equilibrated analytes forms on the solid phase support material. The analytes now equilibrated, both enriched and neutral, are eluted at some time in the future or stored for later analysis as archives. This embodiment produces stable archived equilibrated spike and natural sample that may be shipped, stored or archived.

Another embodiment makes use of the solid phase with the equilibrated analytes and induces ionization directly by surface ionizing the enriched and natural analytes of interest. Ionization methods for surface ionization are some of the following, such as matrix assisted laser desorption ionization (MALDI) or desorption electrospray ionization DESI or laser ablation (LA) or enzyme-linked immunosorbent assay (ELISA) or immunochemical analysis (ICA) or surface-enhanced laser desorption ionization (SELDI).

A method of speeding up equilibration of species-in-solution prior to solid phase separation and high-throughput automation is microwave equilibration acceleration by means of microwave-enhanced chemical methods as opposed to thermal conduction and convection methods. The microwave energy selected from the microwave region such as 2450 MHz produces molecular rotation and ionic conductance of all ions and permanent dipoles that enable faster desorption from surfaces and enhance the ionic and molecular equilibration of natural species and isotopically enriched specie analogues which are implemented during the required sample preparation steps such as extraction and decomposition. These combined sample preparation procedures result in a uniform equilibration of species simultaneously and in much shorter analytical cycle times (sample preparation, manipulation and analysis). This simultaneous extraction and equilibration can be combined with the equilibration steps on solid phase extraction (described above) to enhance both processes. In some instances the analytical cycle time can be reduced from 24 hours to less than 600 seconds. This combined, simultaneous extraction and equilibration step enables ultra fast reactions that are prerequisite specifications for automation of high-throughput applications in hospital, clinical and commercial laboratories, and for near real time applications in homeland security and homeland defense settings.

These new enhancements have been reduced to practice in multiple examples that are disclosed here.

The primary methods disclosed here are pre-absorbed solid phase immobilization of enriched isotope tags, isotopically enriched specie-analogues and natural abundance specie-analogues that are used rapidly to equilibrate species of analytical interest, and microwave-enhanced chemistry significantly accelerated equilibration of isotopic species in solution, or gas form.

Methods of solid phase separation and of microwave-enhanced chemistry have been known but not employed to enhance the efficiency of equilibration, stability, field-use, automation, and storage and delivery of equilibrated species for IDMS and SIDMS.

IDMS and SIDMS methods rely on the measurement of isotope ratios, so problems associated with calibration curves, instrument stability and detector signal drift are negated. The key step, therefore, in these two isotope dilution procedures is the equilibration of the isotopically enriched spike and the analyte present within the sample. When equilibration is achieved, the spiked (isotopically tagged or enriched specie-analogue) material acts as an ideal standard, because only isotope ratios are measured and no external calibration is necessary. This ensures consistently accurate, reproducible measurement of the target analyte. The role of the spiked material as an ideal standard for IDMS and SIDMS also negates problems associated with instrumental drift and matrix effects during mass spectrometric detection, since all the isotopes from the species would suffer from these effects in an identical way. See Ruiz Encinar, J.; Rodriguez-Gonzalez, P.; Garcia-Alonso, J. I.; Sanz-Medel, A. *Trenes in Analytical Chemistry*, 2003, 22(2), 108-114.

If the spike is not fully equilibrated with the sample, a different extraction efficiency for the spike will result, yielding errors in the measurement. For liquid samples, equilibration by gentle agitation should be sufficient, but for the solid samples, equilibration may prove problematic because the analyte can be both absorbed onto the surface and contained within the lattice of the sample matrix. When the species of interest are present in a solid sample and the added spike is in solution, the way to assure isotope equilibration is the quantitative extraction of the original species from the solid into a suitable solvent, where equilibration with the liquid spike is straightforward. See Rodriguez-Gonzalez, P.; Marchante-Gayon, J. M.; Garcia-Alonso, J. I.; Sanz-Medel, A. *Spectrochimica Acta, Part B*, 2005, 60, 151-207.

Clough, R. et. al., have performed the effect of time on the equilibration of spike with the sample analyte for total mercury and methylmercury in two certified reference materials. During their study, they have observed that if the spike is added to the sample and agitated at room temperature (25° C.) with concentrated nitric acid or 50:50 water:methanol (v/v) and 0.01% 2-mercaptoethanol up to 3000 minutes, the equilibration process never reaches 100%. On the other hand, the equilibration can only be achievable if the mixture is heated in a domestic microwave oven for 2 minutes at 650 W. In this case, however, the spiked samples were kept at room temperature for 24 h to allow equilibration before microwave digestion/extraction. See Clough, R.; Belt, S. T.; Evans, E. H.; Fairman, B.; Catterick, T. Anal. Chim. Acta, 2003, 500, 155-170).

Yang, Lu et. al., have found that equilibration takes over 6 hours for chromium species by thermal convection and conduction, delaying the analysis step by a day. The conditions of alkaline at 95° C. used by the authors are chemically the same as the EPA Method 3060A extraction method.

Accurate isotope dilution analysis requires the isotopic equilibration between the spike and the analyte of interest. In order to achieve faster solubilization and stabilization of the spikes and the analytes, organotins and monomethylmercury, as well as faster equilibration, an open focused microwave-assisted extraction procedure was applied in biological samples. The complete solubilization and stabilization was achieved within 5 minutes at 70° C. A 9 minute separation was then accomplished on a GC-MS capillary chromatography column. See Monperrus, M.; Rodriguez Martin-Doimeadios, R. C.; Scancar, J.; Amouroux, D.; Donard, O. F. X. *Anal. Chem.* 2003, 75, 4095-4102; Moreno, M. J.; Arjona, J. P.; Rodríguez-Gonzalez, P.; Homme, H. P.; Amouroux, D.; Donard, O. F. X. *J. Mass Spectrom.* 2006, 41, 1491-1497.

Rodriguez-Gonzalez, P. et. al., have studied different extraction methods, such as microwave assisted extraction, mechanical shaking, alkaline hydrolysis with tetramethylammonium hydroxide (TMAH) and enzymatic digestion for butyltin compounds from biological materials. They have observed extensive degradation of species and lack of equilibration with TMAH and enzymatic digestion. It has been reported that the microwave assisted extraction using acetic acid-methanol mixture produced the best results in terms of low degradation and rapid isotope equilibration and quantitative recoveries. They have also reported in their study that the required complete isotope equilibration was achieved only after the naturally occurring organotin compounds were completely released to the solution from the solid matrix. See Rodriguez-Gonzalez, P.; Garcia Alonso, J. I.; Sanz-Medel, A. *J. Anal. Atom. Spectrom.* 2004, 19, 767-772.

An in vitro gastrointestinal digestion of mussel tissue was performed in combination with species-specific isotope dilution analysis for three butyltin compounds. But in order to avoid any problems derived from the lack of isotope equilibration between the endogenous and the isotopically-enriched spike species, the isotopes were spiked after completion of the digestion process. See Rodriguez-Gonzalez, P.; Encinar, J. R.; Garcia Alonso, J. I.; Sanz-Medel, A. *Anal. Bioanal. Chem.* 2005, 381, 380-387.

Kawano et. al., have studied different heating parameters for the spike equilibration during determination of selenium in biological simples. They have used an in situ fusion just before the pyrolysis stage in order to equilibrate the spike with the sample analyte. See Kawano, T.; Nishide, A.; Okutsu, K.; Minami, H.; Zhang, Q.; Inoue, S.; Atsuya, I. *Spectrochim. Acta*, 2005, 60B, 327-331.

Valkiers et. al., have studied the degree of isotopic equilibration of carbon and oxygen isotopes in a mixture of carbon dioxide gas in the gas phase inside the mass spectrometer during the ratio measurements. See Valkiers, S.; Varlam, M.; Rube, K.; Berglund, M.; Taylor, P.; Wang, J.; Milton, M.; De Bievre, P. *International Journal of Mass Spectrometry*, 2007, 263, 195-203.

Chen, Z and co-workers have studied the time and acid concentration effects on the calcium isotope equilibration in human serum. It is reported in this scientific article that at least 0.22 mol/$HNO_3$ is required for equilibration within 1 h for known sample and at least 6 h time is recommended for unknown samples. See Chen, Z.; Griffin, I. J.; Kriseman, Y. L.; Liang, L. K.; Abrams, S. A. *Clinical Chemistry*, 2003, 49(12), 2050-2055.

Hunkeler, D. and Aravena, R. have studied the direct solid phase microextraction (dSPME) and headspace solid-phase microextraction (hSPME) for extraction and equilibration of carbon isotope ratios in chlorinated methanes, ethanes, and ethanes in aqueous samples and demonstrated that the carbon isotope ratios in the aqueous phase and on the SMPE fiber deviates at least 0.40 by the dSPME and hSPME. On the other hand, for headspace equilibration, molecules in the gas phase were enriched in $^{13}C$ compared to molecules in the aqueous phase by up to 1.46. See Hunkeler, D.; Aravena, R. *Environ. Sci. Technol.* 2000, 34(13), 2839-2844.

Crowther, John R. compiled ELISA methods in The ELISA Guidebook demonstrating how ELISA stationary phases are used to identify proteins, antigens and antibodies by optical methods such as fluorescence and compare them with results done by standard mass spectrometry. The book includes no ELISA method that measures analytes by means of isotopic mass spectrometry. ICMS and SIDMS of ELISA have not been performed for quantitation but comparisons of ELISA to traditional mass spectrometry are prevalent in the literature. See *The ELISA Guidebook* by John R. Crowther, Humana Press New Jersey, 2001.

SUMMARY OF THE INVENTION

A method for the catalyzed equilibration of enriched isotope species and natural isotope species prior to mass spectrometric analysis using solid phase isotope ratio equilibration and measurement is disclosed. The bases of this invention are molecular, elemental and speciated, and quantitative and qualitative sample preparation for definitive qualitative and quantitative analyses of the analytes of interest. The method improves equilibration by utilizing solid phases which have many advantages over liquid and gas phase through simultaneous equilibration and enables automation of IDMS and SIDMS analysis known in the art. The innovation uses solid phases and immobilized enriched isotope reagents, isotopically enriched molecularly manufactured reagents and the process of equilibration on solid and immobilized phases. Algorithms are used to determine mathematically concentrations and directly to correct for species shifts without calibration curves being applied to the mass spectrometric data. Time required to equilibrate and separate the analyte is significantly decreased through sample preparation on solid phases as compared to conventional liquid/thermal equilibration and separation protocols. Reagents and products made for solid phase isotope spiking and equilibration are stable over longer periods of time, thus making it possible to do on-site sample preparation and improve on storage and chain of custody problems associated with degradation of reagents and/or samples while in storage or during shipment. For field workers and laboratory analysts, solid phase isotope spiking and equilibration will make handling of reactive and toxic materials safer in field-spiked and equilibrated forms than they are as bulk reagent solutions, by eliminating several sample preparation and manipulation steps. The sample analyte and isotopically enriched and equilibrated reagent tags are either eluted off for analysis in liquid and/or gas phase analysis or are directly analyzed in solid phase by surface ionization into the mass spectrometer. Solid phase isotope spiking and highly rapid equilibration facilitate the ability to design cost-effective, high-throughput, reliable sample preparation and analysis systems involving high levels of automation and miniaturization sub-systems, thereby making it possible to design highly portable, field-deployable, accurate, low-false positive analytical and detection systems. Such field deployable systems will be highly useful for environmental forensics, homeland security and homeland defense, industrial regulation compliance, biosciences and clinical research and clinical diagnostic purposes. Some of the homeland defense and homeland security applications include multi-point drinking water network monitoring for fugitive agents and air/water/surface analyses in the battlefield for the protection of armed forces. These systems will also be useful for assessing risks of certain diseases in humans as a function of exposure to industrial toxins from the environment and food within the growing field of environmental health. Eventually, such system may turn into tools that will help predict the onset or slow down the progression of certain diseases like autism, some forms of cancer, and immunodegenerative diseases like Alzheimer's, Parkinson's and diabetes. Definitive study using both concepts described above is follows infra.

DETAILED DESCRIPTION OF THE INVENTION

The problem is recently described in a paper from Lu et. al. where they described isotope equilibration in yeast for Cr(VI) and Cr(III) taking up to 12 hours. This data demonstrates a direct solution to this problem. It also describes that individuals skilled in the art do not understand the difference in using microwave and standard thermal methods to equilibrate the isotope and natural species. The paper discusses the use and success of the EPA Method 6800 that we are now taking further in this current work.

Further applications described are that the microwave implementation can be added to microfluidic devices to speed up reactions that are in keeping with this need for faster reactions based on the shorter time frames and very fast reactions. An Agilent chip cube microfluidics devise is shown below that could have for example a coaxial microwave emission to some part of this device to enhance the reaction speed, extraction and/or equilibration for example. Microfluidics using both the column presorbed spiking and microwave enhancement and/or both together are all embraced by the present invention.

Some elemental and molecular species undergo conversion and form other species or the species of interest degrade to other species during sampling, storage, calibration and the measurement processes. Traditional calibration is impossible in many of these cases. Moreover, the accuracy and precision of a quantitative analysis depends on the type of calibration protocols used, e.g. internal standardization, standard addition and isotope dilution, and errors like both fixed and random can be introduced through the use of different calibration techniques. Accurate results using external calibration curve are obtained if the following assumptions are true: calibration standard and the sample have identical matrices; calibration is linear; the analyst prepared the calibration standards accurately within defined error limits; the stability of the standards, however and whoever prepared, is known and are only used within these defined limits of time, matrix, concentration, temperature/humidity, and container material; the measurement of an unknown can only be worse than the uncertainty of the calibration; there are no spectral and/or mass interferences; the sample prepared for analysis involves no positive or negative contamination errors and no sampling errors; and the internal standard behaves exactly same as the sample analyte. See Gonzalez-Gago A et al, J. Anal. At. Spectrom., 2007, DOI: 10. 1039/b705035f; Brown R. J. C., et al, Anal. Chimica Acta, 2007, 587(21), 158-163.

The ICP-MS produces results with a maximum precision (i.e., complex matrices) in the range of 5 to 10%. The main problems associated with external calibration are: stability of analyte in solution; accuracy in sample preparation; purity of calibration standards; choice of internal standard; improper instrumental setup; total dissolved solids; non-spectral interferences; matrix matching; standard addition; sample introduction; chromatographic separation; instrument drift with time; nebulization efficiency; droplet size; physical properties of solution; acid content in the solution; analyst's lack of knowledge/training; background correction; mass bias; dead-time; and isobaric and polyatomic interferences. See Vicki, B. Preparation of Calibration Curves: A guide to best practice, LGC, September 2003.

In order effectively to correct for temporal variations in signal intensity and for systematic variations of the analytical signals in sample and standards due to matrix effects, the physical properties of the internal standards must be carefully matched to those of the isotopes they are applied to. See Hsiung Chiung-Sheng, et al, Clinical Chemistry, 1997, 43(12), 2303-2311; Entwisle, J. American Laboratory, March 2004, 11-14; Eickhorst, T.; Seubert, A. J. Chromatogr. A, 2004, 1050, 103-109.

The standard addition technique is used when the matrix is quite variable and/or when an internal standard that corrects for plasma related effects could not be found. Although the standard addition technique offers better possible solution to matrix interferences through plasma related effects, it requires a linear response. It is therefore very important to work within the linear range for each analyte. See Bonnefoy, C. et al, Anal. Bianal. Chem. 2005, 383, 167-173; Melaku, S. et al, Can. J. Anal. Sic. Spectros., 2004, 49(6), 374-384; Panayot, K. et al, Spectrochim. Acta, Part B, 2006, 61, 50-57.

Protein biomarkers have had tremendous impact in research and on clinical management of human disease, especially cancer. The application of proteomics and genomics to protein biomarker discoveries have enabled hundreds of biomarkers to be identified in a single discovery effort. However, the promise of these discovery tools have not been fulfilled yet due to the lack of quantification and clinical validation. A well functioning enzyme-linked immunosorbent assay (ELISA) can be used at high throughput with extraordinary sensitivity and specificity for quantifying the target analyte. ELISA at the present time is based on colorimetric and fluorescent readers for quantification and is being compared to chromatography and mass spectrometry but has not been combined. See Whiteaker, J. R.; Zhao, Lei; Zhang, H. Y.; Feng, L. C.; Piening, B. D.; Anderson, L.; Paulovich, A. G. Analytical Biochemistry, 2007, 362, 44-54.

Martens-Lobenhoffer, J. et. al., has evaluated the measurement of asymmetric dimethylarginine (ADMA) concentrations in human plasma and serum samples using liquid chromatography mass spectrometry (LC-MS) and compared the results with those obtained from the standard colorimetric ELISA technique. It is reported in this article that the ELISA has produced higher values than the LC-MS, and concluded that the ELISA is matrix dependent. They also concluded that the ELISA overestimated the ADMA concentrations in plasma by a factor of 2. see Martens-Lobenhoffer, J.; Westphal, S.; Awiszus, F.; Bode-Boger, S. M.; Luley, C. Clinical Chemistry, 2005, 51, 2188-2189.

Charissou, A. et. al., has also evaluated the ELISA method for the quantification of carboxymethyllysine (CIVIL) in food samples and compared the results with gas chromatography mass spectrometry (GC-MS) results. During this study they have used both conventional internal standard and isotope dilution internal standard for GC-MS quantification to compare with the standard ELISA. They have reported that the ELISA is a rapid, low cost method with lower detection limit compared to the GC-MS while used with powdered sample. However, using both detection methods on complex matrix like liquid and hydrolyzed infant formulas provided that the ELISA method suffers from lack of specificity and high risk of matrix interference. Otherwise, the two methods produced similar results on powdered milk samples. They have also reported that the ELISA method overestimated the CIVIL concentrations in certain samples with high fat content, such as meat products, and fried foods for which no or low CML levels were detected by GC-MS or HPLC. There might be unspecific interferences of the lipid matrix with the ELISA. See Charissou, A.; Ait-Ameur, L.; Birlouez-Aragon, I. J. Chromatogr. A, 2007, 1140, 189-194. Similar findings were also reported by Scholl, P. F. et al while they were determining the Aflatoxin B1 serum albumin adducts in humans by isotope dilution mass spectrometry and conventional ELISA. They have reported the concentration of AF-albumin adducts measured by ELISA and AFB1-lysine measured by IDMS in 2 mg of albumin were well correlated; however, AF-albumin adduct concentrations measured by ELISA were on average 2.6 fold greater than those of the AFB1-lysine adduct. In this article the authors have hypothesized that the ELISA is measuring other AF adducts in addition to the AFB1-lysine. See Scholl, P. F.; Turner, P. C.; Sutcliffe, A. E.; Sylla, A.; Diallo, M. S.; Friesen, M. D.; Groopman, J. D.; Wild, C. P. Cancer Epidemiol Biomarkers Prev. 2006, 15(4), 823-826.

Wolthers, B. G. et. al., has evaluated the ELISA method for the determination of metanephrine (MA) and normetanephrine (NMA) from human urine and compared the result with those obtained from GC-MS using internal standard and calibration curve but referring to the GC-MS internal standard as IDMS analysis. They have concluded that the ELISA method is capable in the quantification of urinary MA and thus can be successfully used to establish the diagnosis of pheochromocytoma, and also recommended that this simple ELISA method can be executed in any clinical laboratory and hoped that in time it may replace the currently in practice, more complicated, chromatographic techniques. See Wolthers, B. G.; Kema, I. P.; Volmer, M.; Wesemann, R.; Westermann, J.; Manz, B. Clinical Chemistry, 1997, 43(1), 114-120.

From example literature, it is observed that researchers have investigated different samples with ELISA and compared the results with other detection techniques including many mass spectrometric forms e.g. GC-MS, HPLC or IDMS, however turning ELISA into a mass spectrometric procedure has not been developed.

An example of a complete integrated field and/or laboratory system that can be used for Homeland Defense and Homeland Security and or Environmental Forensics is described in a separate section of how all of these components can be combined Section III.

Sold Phase Equilibration, Extraction and Separation Method Enriched Species Bound on SCF column A study done by one of the inventors during preparation of the EPA Method 3200 involved isotopic enriched species of methylmercury adsorbed or chemically attached onto Sulfhydrylated Cotton Fiber (SCF) solid phase column prior to the addition of the sample of certified reference material of mercury species in human hair from the International Atomic Energy Agency (IAEA-085). Data from this study demonstrate the validity of the invention and new method of spiking and equilibrating on solid phase. The results were compared to those of traditional IDMS and SIDMS methods where equilibration was done in solution before the SCF solid phase covalent binding of different mercury species and the sulfhydryl group. The sample was both extracted and spike-equilibrated with microwave energy, then compared with the pre-sorbed solid phase species isotopic spiking and found that both provided accurate data. The example described here involves the processing of two sets of the IAEA-085 reference material human hair as identical samples. Table 1 data from the implementation of the conventional EPA Method 6800, SIDMS, where the sample was spiked with isotopically enriched methylmercury before extraction with microwave energy. Table 2 is from the same standard sample (IAEA-085) and was subjected to the new method of first having the methylmercury extracted using EPA microwave extraction method, EPA Method 3200, without being spiked, and then added to the SCF column where the spike was equilibrated in a solid phase packed as a bed of flow-through medium in a column rather than in solution, as done in current state-of-the-art chemical procedures.

TABLE 1

IAEA-085, Hair Analysis: hair samples were pre-spiked but the SCF columns were not spiked

| Replicate of Sub-sample | Inorganic Mercury ($\mu$g/g) | Methylmercury ($\mu$g/g) | Total Mercury ($\mu$g/g) |
| --- | --- | --- | --- |
| Certified value |  | 21.9-23.9 | 22.4-24.0 |
| IAEA-085-1 | 1.644 ± 0.152 | 21.155 ± 2.986 | 22.799 ± 2.990 |
| IAEA-085-2 | 1.442 ± 0.073 | 21.006 ± 2.367 | 22.448 ± 2.368 |
| IAEA-085-3 | 1.767 ± 0.109 | 22.933 ± 0.496 | 24.700 ± 0.509 |
| Average | 1.617 ± 0.104 | 21.698 ± 0.990 | 23.315 ± 0.995 |

Uncertainties are at 95% CI with n = 4

After analysis using high performance liquid chromatography coupled with an inductively coupled plasma mass spectrometry (HPLC-ICP-MS) and data comparison, it is seen that both processes resulted in 100% recovery and achieved the same accuracy based on the comparison with the certified values of the IAEA-085 standard reference material. These data demonstrate the benefits of the invention by facilitating significant acceleration of the critical steps of delivering the enriched isotope spikes or enriched specie-analogues, and equilibrating them with the species of interest for IDMS and/or SIDMS. The equilibration of mercury species can take place on column or during elution and/or during extraction steps. Equilibration with microwave produce equally accurate results.

TABLE 2

Hair Analysis: SCF columns were pre-spiked with isotope enriched mercury species, but samples were not spiked

| Replicate of Sub-sample | Inorganic Mercury (µg/g) | Methylmercury (µg/g) | Total Mercury (µg/g) |
| --- | --- | --- | --- |
| Certified value |  | 21.9-23.9 | 22.4-24.0 |
| IAEA-085-1 | 1.259 ± 0.027 | 24.339 ± 1.289 | 25.598 ± 1.289 |
| IAEA-085-2 | 1.354 ± 0.030 | 21.224 ± 3.935 | 22.578 ± 3.935 |
| IAEA-085-3 | 1.588 ± 0.015 | 22.736 ± 2.325 | 24.324 ± 2.325 |
| Average | 1.400 ± 0.092 | 22.766 ± 1.301 | 24.166 ± 1.304 |

Uncertainties are at 95% CI with n = 4

After extraction, the extracts were passed through the SCF column (unspiked) to separate the inorganic mercury from the methylmercury, demonstrating the dual-use capability of this invention involving solid phase material for species separation purposes, as well. Then both the eluents (Eluent 1 for methylmercury and Eluent 2 for inorganic mercury, EPA Method 3200 protocol) were analyzed with HPLC-ICP-MS. The deadtime and mass bias corrected isotope ratios were determined and used to calculate the concentration of inorganic mercury and methylmercury using traditional IDMS equations. It is observed from the results in Table 1 and Table 2 that there is no significant difference between the certified values and the measured values in these studies by both compared methods.

From the result in Table 2, it is observed that statistically indistinguishable data were obtained during this study and the results overlapped with the certified values at the 95% confidence interval in Table 1. Moreover, results from both studies were statistically indistinguishable from the certified value and from each other. Therefore, it was concluded that on column equilibration of naturally abundant mercury species with the isotopically enriched mercury species is feasible and has been reduced to practice. This technique produces unbiased and accurate results equivalent to traditional IDMS and SIDMS described in the scientific literature. However, when concentrations are below stability of solutions and limit transportation of the material to the field, from the field or to a remote laboratory or site of low concentrations, the pre-spiked solid phase material or enriched specie-analogues bound to solid phase material is an effective method to implement both IDMS and SIDMS.

Solid Phase Spiking and Equilibration in GC-MS of Alkyl Molecules as Target Molecules Implementing IDMS in the Field.

Solid Phase Stable Isotope Example in Field IDMS with GC-MS Analysis

Certain aspects of the analytical process have not kept pace with the currently available, advanced detection technologies. Chief among them are field sampling (sample collection), chain of custody (sample containment, shipment and storage that minimize or eliminate loss of analyte) and laboratory analysis (sample preparation). Advances in analytical chemistry have led to the development of instruments with detection limits as low as one part per trillion which is well below the stability of aqueous standards. Although many of the chromatographic instrumental techniques have matured and become automated, sample preparation remains one of the slower, labor-intensive and often serially-implemented laboratory processes. The current practice of obtaining and processing of large volumes of sample for each analysis is laborious, time-consuming, costly and unfeasible for rapid transportation and high-throughput analysis. The application of the invention of solid-phase delivery of enriched spike reduces the number of steps and improve field sampling of water, air, drugs, food, agricultural industrial samples, and biological and clinical specimens.

Solid Phase Extraction (SPE) cartridges are packed with stable isotopically tagged speci-analogues presorbed on solid phase material. The modified SPE cartridges are designed for onsite extraction, and prepared specifically for palicular analyte groups. Prepared extraction columns are created with the proper sorbent, bed depth, calibrated reservoir volume, and isotopically labeled analogues. Field extraction is enabled and simplified, requiring minimal sample handling. After field extraction, the SPE cartridge is shipped to the laboratory, where the isotopic standards and analytes of interest are desorbed via elution by an organic solvent. With this method, the analytes and isotopic standards are immobilized on the solid phase media while in transit and storage, without the matrix, where they may be less susceptible to modification and degradation. Analysis is performed with GC-MS using conventional internal standard quantitation, or isotope dilution quantitation. The simplicity of this sampling and extraction protocol enables a streamlined approach to environmental analysis, extending stability, and improving the precision, accuracy, and ruggedness of field sampling and analysis. An enhanced level of quality assurance and quality control is gained in the overall process.

On-site SPE is an extraction method that can be performed in the field and in the laboratory by less experienced personnel. By providing the extraction and/or solid phase with the enriched isotope species, the method can be performed without extensive training, using inexpensive, relatively simple, manual or automated extraction with pre-spiked SPE cartridges. For example, instead of field personnel placing the water sample to be analyzed in a container to be shipped to the analytical lab, the water sample is placed into a calibrated, sample reservoir attached to a SPE cartridge and isotopically equilibrated in the field on the solid phase cartridge. After the sample has been added, it is passed through the SPE media, using either positive pressure, or vacuum. During this extraction process, the organic analytes and species of interest are removed from the water due to relatively strong intermolecular forces of attraction between the sorbent media and the organic molecules. The water that has essentially been stripped of the organic analytes pass through the SPE cartridge. After SPE has been performed, the analytes and isotopic standards are immobilized on the solid phase media without the water matrix, and are therefore less susceptible to modification and degradation that can occur during the period of time when water samples are shipped to the lab, or during storage.

Significant savings of time and resources and suitability for automation through the on-site SPE is demonstrated through several examples. To demonstrate that the field-extracted and equilibrated sample on the solid phase resin remains stable, the cartridges were mailed to test the method after the field extraction has been performed and the sample equilibrated on the solid phase material in the cartridge. Upon receipt of the sample kit containing cartridges with the extracted, on-column equilibrated and immobilized samples, the analytical lab was able easily to elute the bound samples from the cartridges. The analysis can be done by any mass spectrometer.

In the demonstration a GC-MS was used. This invention is a simplified and streamlined sample preparation method that removes several levels of manipulation, each potentially introducing errors due to loss of analyte, incomplete chemical manipulation steps and bias. Further, the invention saves time, money, and enables automation.

Examples of Water Extraction on Pre-Adsorbed Enriched Isotopes in Solid Phase C-18 Cartridges Several types of molecular species results are demonstrated for pre-spiked stable isotope solid phase extraction (PSI-SPE) followed by GC-MS are given in FIG. 1, below. PSI-SPE was performed on the compound classes; oxygenates, and PAG-5, and on the compounds morphine, 1,4-dioxane, and 1,2-dichloroethane. These compound classes are typical for environmental forensic, environmental health and toxicological measurements. The overall results using PSI were found to be statistically indistinguishable to those obtained using conventional laboratory SPE, and certainly within the acceptable ranges for the applicable EPA method specifications.

Example of Oxygenates

Oxygenates are a list of small, polar compounds that are frequently found in gasoline, added to the distillate to enhance combustion process, as an "anti-knock" agent. This list of compounds includes: tert-butanol (TBA), methyl-t-butyl ether (MTBE), ethyl-t-butyl ether (ETBE), diisopropyl ether (DIIPE), and t-amylmethyl ether (TAME). MTBE has been linked to possible environmentally caused health problems. These compounds are particularly problematic because they are highly miscible with water. In the event of a hydrocarbon spill such as refined gasoline, the non-polar petroleum distillate gasoline comes to the surface of a body of water and can be removed or at the very least tracked and the drinking water pumping stations located along the river of a large city temporarily shut down until the gasoline plume passes. This is not the case for oxygenates, which are fully soluble in water. Oxygenates can easily find their way into the ground water, and cannot be readily removed. Further, analysis of water samples to determine concentrations of oxygenate contamination is problematic because of the difficulties involved in extraction of the water sample. The highly polar oxygenates are not readily extracted from the water samples by conventional means. In an effort to increase extraction efficiency, the sample is frequently heated. This has been shown to degrade MTBE into TBA, leading to inaccurate results without SIDMS. Further, MTBE has been shown to degrade into TBA during shipping. This can affect extraction efficiencies and degradation during extraction of oxygenates. The problem has been overcome using PSI-SPE method. Samples of water spiked with oxygenates have been extracted with excellent results, as seen in FIG. 2.

The PAG-5 list of analytes is a group of toxins and pollutants that must be analyzed by many environmental enforcement agencies when closing or monitoring a gasoline-contaminated site. This complex list contains the oxygenate MTBE, the volatile monocyclic aromatics benzene, ethylbenzene, and xylenes, as well as three semivolatile analytes; naphthalene, fluorene, and phenanthrene. This list of compounds, when analyzed by conventional methodologies, must be done using two different test methods; EPA method 8260 for the volatile components, and EPA method 8270 for the semivolatile components. The PAG-5 list of analytes has been done using PSI-SPE using as a single group measured in a single analysis. This greatly reduces the cost of testing. Results for PSI-SPE of the PAG-5 list of analytes is seen in FIG. 6 (PAG-5 using PSI-SPE. SPE Supelco Styrene divinyl-benzene/100 mg. Reagent water spiked with PAG-5 at 20 ppb; Error expressed as 95% CL, n=5).

Morphine

Morphine is a very common drug of abuse. Unlike the previously discussed volatile compounds, the sample matrix of interest for morphine determination is not simply water but a very complex organic matrix. The traditional extraction method for morphine determination by GC-MS is very tedious. PSI-SPE was used for isotopically labeled morphine as a means to speed up the extraction and analysis process, and to provide a more routine and reproducible extraction technique. The SPE results were excellent, as shown in FIG. 3 (SPE Agilent Evidex, 6 ml, 0.5 g; Error expressed as 95% CL, n=4). Morphine was successfully extracted from spiked water and from bovine serum.

Dioxane and Dichloroethane

Another example of small, polar molecule is 1,4-dioxane. This compound is commonly used as a disinfecting agent. While it has not been shown to degrade during extraction or analysis, it is, like oxygenates, very hard to extract from water using conventional means. SPE can, however, be employed in a fashion similar to oxygenate analysis, with very good results. (FIG. 4: 1,4-dioxane and 1,4-dichlorethane. Reagent water spiked with 1,4-dioxane at 2 ppb and 1,4-dichloroethane at 20 ppb. Error expressed as 90% CL, n=3).

The compound Tetrachloroethane (TTCE) has, for years, been a very common degreasing solvent. An example of its usage is in the manufacture of stainless steel tubing. The tubing is lubricated during fabrication with a mid-range hydrocarbon. This lubricant is commonly removed using TTCE. Once TTCE enters the environment, it can be degraded to 1,2-dichloroethane (1,2-DCA), which is far more volatile, and more water soluble than TTCE. It is 1,2-DCA that usually is found as a contaminant in the ground water, and not the parent TTCE. 1,2-DCA is structurally very different from the non-polar aromatic BTEX, or the very polar oxygenates and dioxane. 1,2-DCA has an intermediate polarity, and is a halogenated compound (see FIG. 4). Under SPE conditions identical for that of the extraction of the aforementioned analytes, favorable results can also be obtained for 1,2-DCA.

A problem that can occur when using conventional sampling and analysis methodologies is that of compound losses during transport via microbial or chemical degradation. Many microbes are capable of consuming pollutants as a food source. If this occurs during transportation of the sample, the analyte losses cannot be determined, and the accuracy of the measure is compromised. A study was performed to evaluate if degradation could take place on the SPE cartridge after the sample has been extracted and equilibrated on the resin. Natural water samples were taken from a monitoring well, analyzed and found to contain a number of contaminants. The sample was extracted and analyzed via SPE and PSI-SPE at day 0 (day 0 indicating 0 days had elapsed between the sampling event and the extraction/analysis). A portion of the same sample was allowed to remain in a sealed bottle at room temperature for a period of 14 days, to see if any losses due to biodegradation occurred. A portion of this same sample was also extracted at day 0, but not eluted from the SPE cartridge until day 14, to see if degradation comparable to that which occurred in the sealed bottle would also occur on the cartridge, once the analytes and microbes have been removed from their aqueous environment and isolated on the cartridge. The results of this study are shown in FIG. 5. (Effects of biodegradation on monitoring well sample. All concentrations in ppb, Error expressed as 90% CL, n=3).

As seen in FIG. 5, the initial concentrations of contaminants extracted and analyzed on day 0 are within good agreement using either SPE or PSI-SPE. Analysis after allowing the sample to remain in a sealed bottle for 14 days indicate complete degradation of all analytes, with the exception of MTBE. MTBE can be degraded by a relatively few types of microbes, and its degradation was not anticipated in this sample set. Analysis of the sample that was extracted on day 0, but not eluted from the cartridge until day 14 reveals no degradation of the compounds of interest. This study indicates that water samples containing pollutants will undergo degradation when sampled in their sample matrix and kept without any additional steps, but not when separated and stored on an SPE cartridge. This is another example of the utility of on-site PSI-SPE.

Calibration and Comparison with Pre-Spiked Isotopes on the Solid Phase

In conventional environmental analysis, for both volatile organic analytes (VOA) and semi-volatile organic analytes, the SVOA analysis (EPA Methods 8260 and 8270), quantitation is performed based on response factors generated from a calibration standard. The standard uses an analyte of known concentration that is created using internal standards and the analytes being tested for. The solvent for this standard is the same as the elution solvent. In a method that utilizes calibration standards, errors in quantitation can occur if the extraction efficiency for the analyte of interest in the sample mixture is less than 100%, and not corrected with the internal standards. Since the calibration standard itself does not go through the extraction process, analyte extraction inefficiency will result in a diminished signal, relative to that of the non-extracted calibration standard. Errors can be compounded when, in the PSI method, the internal standards presorbed on the column are either 1) not bound to the extraction media as tightly as the analytes being extracted (breakthrough), resulting in falsely elevated concentrations, or 2) bound more tightly to the extraction media than the compounds being extracted (retainment), resulting in falsely diminished concentrations. Both of these types of errors can be negated through the use of a calibration cartridge. A calibration cartridge is an SPE cartridge that has been prepared in the same manner as the sample cartridge, with internal standards presorbed on the solid phase material. To create a calibration cartridge, clean reagent water is spiked with a quantitative amount of the calibration compounds. This is done by the analyst at the time of sample extractions, by breaking a sealed glass ampoule of calibration solution, and adding it to clean reagent water. This calibration sample is now extracted using PSI-SPE in the same fashion as the samples. When this cartridge is eluted, the extract serves as the calibration standard. Because this type of calibration standard has been through the same extraction procedure as the samples of interest, responses generated from it have now been corrected for extraction efficiencies of less than 100%, resulting in superior data. Results comparing quantitation using a conventional calibration standard and a calibration cartridge are shown in FIGS. 6 and 7.

Comparison of Response Factors

The response factor is the ratio of the area of a compound to the area of its isotopically labeled analog, a given concentration. If the response for both of these analytes is identical, throughout the extraction and analysis processes, the area counts should be identical, and the response factor therefore equal to 1. In practice, however, the responses will vary slightly for a compound and its isotopically altered analog, due mainly to non-perfect mass measurements when preparing the standards, the response factors, in reality, are very close to 1.0. If the response factor for a compound is one, or sufficiently close to assume a value of 1.0, quantitation and even analysis becomes much easier. In fact, if the response factor can always assumed to be 1.0, there is no longer any need to prepare and run a calibration standard. If this is the case, it would radically change the manner in which analysis is performed. A comparison of how closely the values of a spiked water sample quantitated using a response factor, versus quantitation assuming a response factor of 1.0 for one semivolatile compound, naphthalene, and one volatile compound, benzene, can be seen in FIG. 8 (RF Comparison. Calibration RF vs. RF=1. SPE Supelco Styrene divinylbenzene/100 mg. Reagent water spiked with PAG-5 at 20 ppb; Error expressed as 95% CL, n=5. RF Naphthalene=1.036, RF Phenathrene=0.999). The results for the comparison are very good, sufficiently so to indicate that a more extensive study should be carried out.

Potential for Automation

The potential to use PSI-SPE as a means to allow for automation is an attractive goal which will influence the design of automation features in future instrument systems designs. The following is a sampling of a few areas where automation in one form or another can be employed using PSI-SPE. For environmental forensic and environmental health monitoring, there are a number of opportunities to apply this technology. Monitoring drinking water, fresh water or wells, located on sites that have been determined to be contaminated or to monitor for contamination continuously with routine sampling are all opportunities to automate the sampling due to the long term stability of these solid phase pre-spiked materials. PSI-SPE could be employed and/or could be duplicated on a manifold system, where prepared cartridges are mounted. Through the use of solenoids and switching valves and standard automation apparatus, sampling could be regularly performed at a predetermined time. Flow from a sampling stream could be diverted through the cartridge, for the appropriate amount of time, and then the flow of sample replaced with a stream of dry air, to remove residual water after PSI-SPE sampling component. With the extraction complete, the samples are stable for long periods of time or can be immediately removed and the sample cartridge analyzed on site or transported or even mailed to an analytical lab. Duplicate samples can be distributed for a variety of MS analysis and also archived for long-term Quality Control (QA) and validation.

Food, Beverage and Consumable Analysis

The Food and Drug Administration (FDA) and several independent organizations have identified low levels of benzene in a number of soft drinks and fruit drinks. Research indicated that at low pH, the benzoate ion, used as a preservative, reacts with ascorbic acid (added vitamin C) to form benzene. Benzene is a known carcinogen, and is regulated by the EPA. Any concentration of benzene in waste water above 5 ppb is considered hazardous. Inventors' own survey of existing products showed a number of drinks had benzene concentrations in excess of 5 ppb. While the mechanism of formation is not yet fully known, it appears that heat, light, and certain trace metals, as well as ascorbic acid contribute to the conversion of the benzoate ion into benzene. It is suggested by the FDA that formation of benzene may be a function of shelf life and temperature conditions after the bottled drink has reached the store. This is an example of where PSI-SPE and duterated benzoic acid enriched isotope standard would be too low in concentration to be stable in liquid standard form but would be stable presorbed onto the solid phase. Other drugs and toxins desired to be analyzed by the FDA or Homeland Security could also be presorbed in enriched isotopic form and be a valuable new analytical tool for qualitative and quantitative analyses. It is therefore important to find a method to perform rapid, inexpensive, routine monitoring of water, beverage, foods, pharmaceuticals and other sample streams for contaminant and toxins similar to this examples using benzene in a timely manner to use in manufacturing, quality control and in homeland security and homeland defenses scenarios. PSI-SPE could cost-effectively be performed through the use of automated manifold systems as a stand alone device or a front-end module of a completely integrated, automated analytical measurements system.

Comparative Study of SPI-SPE with Normal Analytical Methods

A time study was performed to provide an example of the time savings that could be realized using pre-spiked stable isotope solid phase extraction (PSI-SPE). This study focused on a set of ten water samples analyzed for semivolatile analytes using EPA Method 8270 as the determinative method, and EPA Method 3510 as the extraction method. Results are shown in Table 3.

TABLE 3

Time study of a set of ten water samples.

| Process | Conventional (hrs) | Tested (hrs) |
| --- | --- | --- |
| Sampling | 0.67 | 0.33 |
| Shipping | 0.50 | 0.08 |
| Log in | 0.33 | 0.08 |
| Extraction | 0.83 | 0.25 |
| Extract Prep | 0.33 | 0.00 |
| Analysis | 1.33 | 1.00 |
| Data Process | 1.5 | 0.58 |
| Forms/Report | 1.00 | 0.08 |
| Total | 6.49 | 2.41 |

The PSI-SPE results in significant time-savings. Processing the samples from field to finished result was performed in 37% of the conventional methodology. Quality of data was superior to those obtained by means of the conventional protocols.

Economic Evaluation

A cost study was performed to obtain a basic understanding of the cost savings that could be realized using PSI-SPE. This study focused on a set of ten water samples analyzed for semi-volatile analytes using EPA Method 8270 as the determinative method, and EPA Method 3510 as the extraction method. Results are shown in Table 4.

TABLE 4

Cost study of ten water samples

| Process | Conventional ($) | PSI-SPE ($) |
| --- | --- | --- |
| Sampling | 6.70 | 3.33 |
| Shipping | 5.00 | 0.83 |
| Log in | 3.33 | 0.83 |
| Extraction | 9.96 | 2.50 |
| Extract Prep | 5.28 | 0.00 |
| Analysis | 21.28 | 16.00 |
| Data Process | 24.00 | 9.28 |
| Forms/Report | 12.00 | 1.33 |
| Total | $87.55 | $34.10 |

The QCS as described above, utilizing on-site PSI-SPE, resulted in a significant cost-savings. Processing the samples from field to finished result was performed at a cost 39% lower than the conventional methodologies. The savings will be much greater through economies of scale when products and devices based on this invention are made and marketed in large quantities.

Comparison of Samples Split for Comparison

A set of real world samples were acquired and split with an outside laboratory, to compare the results. Four samples were taken from a contaminated site that is in the process of being re-mediated for gasoline contaminants. The samples were sent to a commercial laboratory for conventional analyses, and were also processed using on-site PSI-SPE. The results were shown in Table 5.

TABLE 5

Monitoring well samples split with a commercial environmental laboratory

| | Comm. | PSI-SPE | Comm. | PSI-SPE | Comm. | PSI-SPE | Comm. | PSI-SPE |
| --- | --- | --- | --- | --- | --- | --- | --- | --- |
| Sample Name | MW-9 | MW-9 | MW-10 | MW-10 | MW-16 | MW-16 | MW-19 | MW-19 |
| Benzene | 54 | 45 | <5 | <5 | 7 | 8 | 58 | 45 |
| Toluene | <5 | <15 | <5 | <5 | <5 | <10 | <5 | <10 |
| Ethylbenzene | 76 | 59 | <5 | <5 | <5 | <5 | <5 | <5 |
| Xylenes | <10 | <50 | <10 | <10 | <10 | <10 | <10 | <10 |
| Naphthalene | 6 | 6 | <5 | <5 | <5 | <10 | <5 | <10 |

Analytes of interest were detected in monitoring well #9 (MW-9), monitoring well # 16 (MW-16), and monitoring well #19 (MW-19). The identities of the analytes, as well as the determined values were all in close agreement between the two methods.

Presorbed Stable Isotope Solid Phase Demonstration Conclusions

Presorbed Stable Isotope—Solid Phase Extraction has been shown, by reducing it to practice, to be an effective method of sample extraction and equilibration. PSI-SPE will remove many sources of error inherent in current laboratory extraction methods and be the basis of automation that will result in the design of novel, efficient, reliable, rapid sample preparation devices and systems.

Solid Phase ELISA and SELDI Isotope Dilution and Speciated Isotope Dilution Mass Spectrometric ELISA—the most popular immunoassay Mammalian immune reaction starts with the recognition of a compound that the immune system cannot recognize (antigen) by a particular special groups of cells (B cells). Then, the immune system starts producing antigen-specific B cells that produce specialized proteins (antibodies) with specific properties to bind to the antigens. Once bound, to the antigen, the B cells then facilitate a series of reactions that aims to eliminate the antigen, as soon as possible. Immunodiagnostic assays (immunoassays) use this host defense proteins (antibodies) to detect foreign substances, such as viral antigens, directly in the person's blood. Immunoassays are a group of highly specific protein binding assays in which the antigen recognition properties of antibodies are utilized. The most popular immunoassay used today is the ELISA (Enzyme Linked ImmunoSorbant Assay) method. The key to all ELISA systems is the use of antibodies. Antibodies are produced in animals in response to antigenic stimuli. Antibodies are specific biochemicals that bind to the antigens used to detect particular antigens used for their production. Thus, they can be used to detect particular antigens if binding can be demonstrated. Conversely, specific antibodies can be measured by the use of defined antigens, and this forms the basis of many assays in the immunochemical research and diagnostic biology fields.

The basis of quantitation relies on the enzyme-generated signal to be proportional to, or in linear relationship with the concentration of antigen. Advantages of ELISA are simplicity, ease-of-reading (by eye or a device), rapidity, sensitivity, commercial availability of reagents, kits and instruments, adaptability, analyst and laboratory safety, safe disposal, relatively easy standardization and quantitation.

Using laser ionization, direct and quantitative solid phase IDMS and SIDMS mass spectrometric measurements are accomplished by incorporating the isotope to the solid phase surface modified material so that when Matrix Assisted Laser Desorption Ionization (MALDI) or Laser Ablation (LA) remove both that surface and or matrix, and the analyte direct enriched isotopic ratio analysis are done. At this point, another dimension of quantitation is added with one additional degree of freedom not present previously. This final degree of freedom permits ratios instead of quantitative removal of a surface solid state equilibrated system to impart the mathematical advantages of IDMS and SIDMS. One key advantage is that, for achieving definitive quantitation and reproducibility, removal of the entire modified solid phase surface/matrix (containing the isotopically enriched tag) and analyte are not required. Under IDMS and/or SIDMS conditions, any portion of the modified solid phase surface/matrix (containing the isotopically enriched tag) will permit quantification based on isotopic ratios and not calibration curves. Achieving quantification without the calibration curve is unique for IDMS and SIDMS, as other forms of MALDI or LA require quantifiable and reproducible removal of the surface to produce calibration curves. Here, any portion of the equilibrated surface yields accurate quantification and precludes errors normally associated with both mass spectrometry quantification and ELISA quantification. Once equilibrated, variations in the matrix adsorption and removal efficiency are not longer factors in quantification. Mass spectrometer efficiency in transporting ions though the mass spectrometer mass analyzer and signal drift are eliminated as sources of error in quantification in the IDMS and SIDMS methods. The solid phase spiking (tagging) enables direct mathematical quantification as described in IDMS and SIDMS previously not applied in the field of ELISA and or mass spectrometry.

Application of ELISA using fluorometric quantification, have recently begun in the environmental health and environmental forensics fields. ELISA has been employed for chemical analysis of triazine, sulfonylureas, organophosphates, polychlorinated biphenyls (PCBs), cyclodienes, and BTX (benzene, toluene, xylene) and other toxins for bioanalytical analysis and verification of waste sites by the US EPA and environmental contractors. Some of the challenges that restrict widespread use of ELISA in the environmental field are detection limits, calibration curve errors and matrix interferences. These issues and multiple sources of errors weaken legal defensibility of ELISA-produced data in the environmental health and forensic fields, where often analytical data are evaluated by experts in legal proceedings. The solid phase equilibration and direct quantification without calibration curves through IDMS and/or SIDMS are dramatic improvements in legal defensibility because of the definitive quantification methods using solid phase equilibration mass spectrometry and definitive direct algorithmic quantification. Incomplete and partial recoveries of the matrix and analyte, fluctuations in ionization, instrument inefficiencies, performance degradation and other sample manipulation or instrument oriented biases are inconsequential to accuracy due to the use of equilibrated isotope ratios. Hence, these normally present biases are all simultaneously reduced or eliminated, thereby enabling a stronger position in the courts for data defense.

ELISAs can be carried on in several formats on a variety of solid support material produced in different shapes and packages. By far, the most popular ELISAs utilize plastic microtiter plates in an 8×12 well format as the solid phase. Hence, an ELISA test can be done in each of the 92 individual wells in a microtiter plate (see FIG. 9).

In order to create a useful ELISA, three criteria must be met:

Dilution Linearity: This is closely related with the next step, recovery rate. When signal (expressed as peak area, peak area or intensity) vs dilution factors plotted on an x-y chart, it must produce a straight line.

Recovery Rate: This is the percent of the concerned material observed after the assaying when a known quantity of the concerned materials is added into the assay reaction. The recovery rates should be within 10% for the clinical routine work.

Percent recovery rate={(Estimated value)−(Added value)}/(Added value)×100

Intraassay and interassay variation: The intra-assay means values in one ELISA plate and the inter-assay means values between different plates, usually carried out at different dates.

ELISA Types and Systems

Fundamentally, there are two types of ELISA: Competition (C-ELISA) or Inhibition (I-ELISA). The terms "competition" and "inhibition" describe assays in which measurement involves the quantitation of a substance by its ability to interfere with an established pre-titrated system. The systems can also be used for the measurement of either antibody or antigen.

From a methodology perspective, there are three basic ELISA systems that all ELISA tests (both C type and I type; direct or indirect) are based on:

Direct ELISA. Antigen is attached to the solid phase by passive adsorption. After washing, enzyme-labeled antibodies are added. After an incubation period and washing, a substrate system is added and color is allowed to develop.

Indirect ELISA. Antibodies form a particular biological species react with antigen attached to the solid phase. Any bound antibodies are detected by the addition of an antispecies antiserum labeled with enzyme. This is widely used in clinical diagnosis.

Sandwich ELISA. This system involves the antibody or the capture antigen attached to a solid phase material.

Direct sandwich ELISA. If it is a direct sandwich assay, the detecting antibody is labeled with enzyme. The antigen is detected using serum specific for the antigen. The detecting antibody is labeled with enzyme. The capture antibody and the detecting antibody can be same serum or serum from different animals of the same species or from different species. The antigen for a direct sandwich assay must have at least two antigenic sites.

Indirect sandwich ELISA. If the system is an indirect sandwich assay, the antigen is captured by a solid phase bound antibody. Antigen is then detected using antibodies from another species. This, in turn, is bound by an antispecies conjugate. Thus, the species of serum for the coating and detecting antibodies must be different; the antispecies conjugate cannot react with the coating antibodies.

The most commonly used enzymes are horseradish peroxidase (HRP) and alkaline phosphatase (AP). Other enzymes, such as β-galactosidase, acetylcholinesterase and catalase have also been used, but limited substrate options, limited their widespread applications. A detection enzyme may be linked directly to the primary antibody or introduced through a secondary antibody that recognizes the primary antibody. It may also be linked to a protein such as streptavidin if the primary antibody is biotin labeled. The choice of substrate depends upon the necessary sensitivity level of the detection and the instrumentation available for detection (spectrophotometer, fluorometer or luminometer). Among all protein labeling and visualization techniques, the well-understood biotinylation is the most popular one because of the simplicity of the labeling and spectrometric measurement and the high specificity and selectivity of avidin (a glycoprotein found in the egg white and tissues of birds, reptiles and amphibia) with the small vitamin, biotin. Avidin-biotin reaction is the most useful tool in assay systems designed to detect and target biological analytes. The extraordinary affinity of avidin for biotin allows biotin-containing molecules in a complex mixture to be discretely bound with avidin conjugates.

Mass Spectrometric ELISA Microarray Chips Using IDMS and/or SIDMS

Although mass spectrometers and isotopic measurement techniques are highly desirable as potential immunoassay detection systems because of their inherent high sensitivity and significantly lower interferences, they have not been successfully used as the definitive quantitation detector for ELISAs because of a number of obstacles. Chief among them are the high cost of the mass spectrometers, instability of the mass spectrometer detector signal and lack of expertise among the biological scientists about isotopic analysis and relatively recent popularity of mass spectrometers in the field of bioanalytical measurements.

Use of enriched isotopic tags or isotopically enriched synthetic peptides mimicking the antigenic sites or antibody are feasible for ELISA type of assays when these peptides are placed in discrete sample spots arranged as rows of bound-antigens or immobilized antibodies in microarray plates. The microarray plates are then be processed and introduced to the mass spectrometer for liquid and/or gas ionization and definitively quantitative mass spectrometric analysis.

Whole cells, live or attenuated, with isotopic tags incorporated through nutrients in the media during fermentation or through a chemical isotopic tagging process can be used when the cells with the can immobilized on solid phase matrices are immobilized and provide as antigenic lattices. Such cells are enclosed in specially designed multi-array chips with discrete sample holding sites having the ability to keep the cells bound and viable for the duration of the analysis cycle in the mass spectrometer.

The isotopic analysis methods using the principals of IDMS and/or SIDMS and the inventions described herein are used for capture and analysis of biomolecules, by immobilizing ligands, such as lectins, polysaccharides, nucleotides, biomolecule and/or chemical toxins that can be isolated from a natural source or synthesized as functional analogues, with affinity for other biomolecules. Enriched isotopes can be used for visualization of each of the thousands nucleotide probes that are immobilized on the gene-chips microarrays.

Embodiments of the invention of enriched isotopically tagged antigens on surface modified solid phase material are shown in FIGS. 10, 11, 12.

Mass Spectrometric SELDI Analysis using IDMS and/or SIDMS

One of the recent applications of mass spectrometry in the clinical diagnostic involves SELDI (Surface Enchanced Laser Desorption Ionization) chips with various different functional surfaces for immobilization of proteins and peptides which are used for protein expression profiling. These chips utilize immobilized biomarkers from a cellular sample source where these biomarkers are uniquely expressed in response to a disease condition. The entire field of biomarker analysis and protein expression profiling has been hampered by lack of definitive, direct quantitation and reproducibility, as efforts to-date have utilized direct proteomic analysis that, so far, does not involve any molecular tags for definitive quantitation purposes. Enriched isotope tags overcome these limitations by providing a means to measure isotopically tagged biomarker ratios on a SELDI protein chips, vastly improving quantitation and reproducibility through IDMS and/or SIDMS quantitation. See FIGS. 13, 14 and 15.

Direct Tissue Profiling Using IDMS and/or SIDMS

New molecular profiling technologies aid in analysis of small pathologic samples obtained by minimally invasive biopsy, enabling the discovery of key biomarkers synergistic with anatomopathologic analysis related to prognosis, therapeutic response, and innovative target validation. Thus proteomic analysis at the histologic level in healthy and pathologic settings is a major issue in the field of clinical proteomics. Direct tissue proteomic analysis (DTPA) is an original application of SELDI-MS technology that can expand the use of clinical proteomics as a complement to the anatomopathological diagnosis. The DPTA method offers unique high-throughput characteristics that can be used for biomarker discovery in large cohorts of patients.

The DPTA approach has been used for classification of diseases such as lung carcinoma and brain tumors thus enhancing anatomopathological diagnostic techniques. The DPTA is a recently developed fast, sensitive technique that opens the door to new perspectives in clinical proteomics. Current developments in this area, addressing the needs for definitive quantitation, reproducibility and sensitivity are achieved through the use of enriched isotope tags and application of the principles of IDMS and/or SIDMS introduced as solid phase surface modified or unmodified media.

Direct Mathematical Deconvolution is Necessary as Only Direct Mathematical Solutions Will Permit Quantitation of Analytes in Environmental Forensic, Environmental Health and Homeland Security Measurements—Examples of the Practice Reduced to Practice As has just been demonstrated with the mercury species in human tissues, a calibration curve could not be used to quantify as over 80% error would have resulted. Only SIDMS direct enriched isotope calculations can both quantify and correct for species conversions of species transformations. It has been discovered that IDMS and SIDMS both must be calculated directly by mathematical algorithms and calibration curves should not be used to avoid errors that are common in the analytical laboratory and which are critical and are time consuming and moreover unacceptable in critical measurements such as homeland security, environmental health and industrial measurement.

Enriched isotopic analogues of analytes of interest are created from primary enriched isotopes or are purchased or synthesized in the laboratory. The application of IDMS and SIDMS coupled to various methods of ionization such as ESI, nanoESI, nanochipESI, DESI, MALDI, LA, SELDI, APCI, ICP, GC-ICP, GC-MS are embraced by the present invention. For demonstration purposes both GC-ICP-MS and nanoelectrospray Time of Flight mass spectrometry are shown. Examples in both GC-ICP-MS and Ionization by nanochipESI coupled to time of flight mass spectrometry (nano-chipESI-TOF-MS) platforms are used to demonstrate examples appropriate for homeland security, environmental forensics, environmental health, and industrial sample measurement scenarios. Demonstration of toxin data are attached for mercury species, sodium azide, and potassium cyanide.

The mathematical algorithms necessary for the quantitative determination of target analyte species using spiking for IDMS (Isotope Dilution Mass Spectrometry) and SIDMS (Speciated Isotope Dilution Mass Spectrometry) are different than traditional methods (and new applications of mathematical methods) as they can only be accomplished by direct mathematical solution are required. Calibration curve from a pure standard are not possible in a single measurement or may not be able to be used at all. These reductions to practice are developed and applied to many types of enriched isotopic sample preparations such as direct solution ionization and surface adsorption, bonding, ion exchange, solid phase extraction measurements and many others.

The first example of a measurement that cannot be quantified by calibration curve and that must be accomplished by SIDMS measurement is a blood sample with methylmercury and inorganic mercury and also spiked for ethylmercury. This sample was separated and ionized after equilibration with separate isotopic analogues of inorganic, ethyl and methyl mercury. In this example inorganic mercury, $Hg^{+2}$, is spiked with 98% enriched inorganic mercury $Hg^{+2}$-199 and methylmercury ($CH_3Hg^+$) is spiked with methylmercury $CH_3Hg^+$-202 and ethylmercury ($C_2H_5Hg^+$) is spiked with $C_2H_5Hg^+$-201 and metallic mercury species)($Hg^0$) is not in the original sample and is created by the thermal decomposition in the GC column used to separate the three mercury species. FIG. 16 below demonstrates that a calibration curve would be difficult if not impossible to use as different amounts of both inorganic, methyl and/or ethyl mercury in human blood or urine would produce different amounts of all four species (inorganic, methyl, ethyl and metallic mercury) in different proportions and no calibration curve could be established for unknown individual samples. Only mathematical deconvolution by SIDMS methods can permit quantitation in such cases. As in the example above for human hair and the 6 separate transformations that are described there in this example there are at least 4 more that would have to be evaluated and corrected for as it is not only the formation of the fourth species of metallic mercury here but also the contribution to this fourth species by the transformation of inorganic mercury, methylmercury, and ethylmercury.

These cases are more prevalent than once thought and are common in many types of analysis of reactive species such as mustard gas, pesticides and pesticide metabolites, cocaine and the metabolic product in the body which is morphine. Many of these molecular shifts are needed to be quantified but are not amenable to accurate or rapid quantification if calibration curves are the method used to quantify.

IDMS, SIDMS and Direct Species Algorithms Depend on the Species Generated and Only Direct Mathematical Algorithms Newly Derived for Idms and Sidms Analysis can be Used for Quantification of Dynamic Systems.

The enriched stable isotope spike ("spike") must have a different isotopic composition from the sample but the same chemical form and chemistry of the analyte(s) of interest. The matrix composition of the actual sample and the normal standards are rarely the same and any difference in the composition of other elements makes for different isotopic analogues being expressed in soft ionization methods such as ESI, nanoESI, nanochipESI, MALDI, SELDI, and APCI. Thus there cannot be any calibration curves that will represent the sample accurately. An example is presented here for sodium azide and potassium cyanide.

The spike is prepared either in aqueous and/or acid and/or in organic solvent solutions, or fixed to a surface by adsorption, ion exchange or bonding. Calibration by establishing a calibration curve can not be accomplished in soft ionization methods such as ESI, nanoESI, DESI, MALDI and SELDI or in hard ionizations such as ICP-MS as in the above mercury species example. In soft ionization methods the ions being measured and quantified is dependent on the matrix with the analyte in the real sample and can not be simulated by a standard or even a standard attempting to matrix match. The ion is a product of the matrix interactions simultaneously. The analyte may have many representative molecular ions and ion species that are represented in the mass spectrometer. Azide will be used as an example to show several representations based on the matrix and sample conditions. Each representation requires different mathematical quantification using IDMS and SIDMS directly. Soft ionization does not produce molecular ions independent of the matrix but incorporate the matrix and environment to change the concentration of which molecular ions and isotopically enriched analogue ions are expressed. Examples are provided below. Calibration curves and the use of standard IDMS and SIDMS equations can not be used to quantify but quantification is possible only by using new mathematical algorithm protocols for these isotopic species from soft ionization. As you can see the standard IDMS equations do not account for multiple expression and simultaneous and different isotopic ratios for quantification.

The general mathematical equation for the quantitative determination of the isotope ratio in IDMS is shown in Equation-1 and the direct algorithm for a mathematical solution to determine the concentration of an unknown sample is a rearrangement of this equation and is shown in Equation-2. The individual components of this direct mathematical solution is presented below in Equation-2.

$$R_m = \frac{A_x C_x W_x + A_s C_s W_s}{B_x C_x W_x + B_s C_s W_s} \quad \text{Eq-1}$$

$$C_x = \left(\frac{C_s W_s}{W_x}\right)\left(\frac{A_s - R_m B_s}{R_m B_x - A_x}\right) \quad \text{Eq-2}$$

Where $W_x$=weight of sample $W_s$=weight of isotopic spike $C_s$=species concentration in the spike (enriched)

$C_x$=species concentration in the sample (unknown)

$A_S$=atom fraction of altered isotope A in the spike (enriched)

$A_x$=atom fraction of isotope A in sample (natural)

$B_s$=atom fraction of altered isotope B in the spike (enriched)

$B_x$=atom fraction of isotope B in the sample (natural)

$M_x$=average atomic mass of the species in the sample

Ms=average atomic mass of the species in the spike $R_m$=measured isotope ratio of isotope A to isotope B (enriched/natural)

The use of calibration curves is also prohibited by sifting species concentrations that are dependent on dynamic species concentrations and matrix of the sample that can not be duplicated by standard calibration solutions run separately. Soft ionization methods such as ESI, nanoESI, MALDI, APCI, and EI are examples of some of these molecular soft ionization sources that are most susceptible to complex molecular ions that can not be duplicated in standard solutions without the matrix. Dynamic species and species that are determined by the sample matrix itself using soft ionization methods require very different mathematical treatment than hard ionization methods such as ICP-MS that reduce all species to elemental ions and may use calibration curves because of the elimination of matrix effects and molecular information due to harsh ionization.

This application is not adequate to quantify the various expressions of molecular ions of soft and complex ionization. In this example Azide is used in, both positive and negative ion mode. Sodium (Na) ions are in this pure solution with Na added as the positive ion influence and ratios of 1:1 for one of the species in positive ion mode and 1:2 or 1:3 in negative ion mode are both expressed simultaneously. Whatever ion is available and dominant such as K would also be represented by a molecular ion that is only present in the actual sample with the matrix conditions of that sample. Matrix matching of a calibration solution can not accurately or completely account for the concentration and complexity of the exact conditions of matrix ions that are in the real sample. Further ion modes are present as shown in FIGS. 17 though 24. Only multiple algorithms can take into account many of the ion expressions that are necessary to quantify the azide in this first set of examples. In positive ion mode one set of species ions are reveled and in the negative ion mode a second set with distinctly different ratios are observed (see FIGS. 17 though 20).

The direct calculation without bias in an accurate quantification of multiple species of isotopically enriched and natural toxin separated by the mass spectrometer by mass is an extension of IDMS and SIDMS as the species are different subspecies from the same parent species. The deconvolution in these cases is not of multiple species that are transforming but of multiple species that are created from the same species in solution or in solid phase and expressed in unique ratios and patterns. Mathematically the quantification must take several species and their distinct ratios into consideration accurately to quantify the toxin. FIG. 21 demonstrates multiple sections of the charge to mass ratio (m/z) mass spectrum that provide over a dozen confirming ratios in distinct species created by this matrix with Na and as many would be split between K and other ions and Na and K ions would be produced if K were in the sample. In this case the Na4(N3)5- ion would also have Na3K, Na2K2 and NaK3 and K4 analogues. Each of these would be distinct and would be different from a calibration done on a pure standard. Only by applying direct mathematical solutions to the actually isotopically tagged real species that are created in situe are the real samples quantified. Only direct mathematical isotopic ratios can be used as no accurate representation of the actual analyte species expressed by the sample and its isotopic analogues can be expressed without the matrix and the real sample present. Accurate concentrations are possible to 2 and 3 significant figures using isotopic ratios but less than 1 significant figure could be produced in a complex matrix from a simulated calibration standard in the majority of cases and these are not practical on a working basis.

These multiple related species being produced from natural and isotopic enriched species are prevalent in soft ionization such as nanoESI and MALDI and disappear in harder ionizations due to stability of the ions. Another example is a toxin potassium cyanide such as in FIG. 24.

In a matrix with any other amount or mixture or component of metal ions (such as K or any metal ion that would be chelated by the $CN^-$ chelate) the anion chelators would express the Fe, Cu, Ni, Cd, Hg in the spectrum will be modified and will be completely different and is impossible to predict theoretically at the present time. For example the actual sample will have a formation constant and stepwise formation constents with mathematical stabilities that are multiplicative such as for $Hg2+$ $Cd2+$ for K1, K1K2, K1K2K3, K1K2K3K4 of 5.5, 5.1, 4.6, 3.6 for and 10.0, 16.7, 3.8 and 3.0 for the Log of Ks for Hg and Cd ions respectively with the cyanide negative ion. All of these would be in competition and are uncalculatable and must be measured with calibration cures being set up to quantify real samples impossible to predict. Only a calibrationless direct mathematical solution is possible in these complex soft ion molecular quantifications. There could be over 80 factorial possible combinations of ions that could possibly be expressed in a water solution.

The use of traditional calibration curves in the normal context of the term is not applicable. The use of calibration curves, use of internal standard using calibration curves or calibration curve based on these ions is appropriate and can be constructed in a manner quantitatively meaningful of concentration of the unknown matrix of a real sample from a pure calibration standard. If potassium and sodium and other ions are present there are potassium and sodium and other metal adduct ions expressed and complex species created that are related to the parent toxin but are new species expressed in the mass spectrometer based on the sample matrix, sample preparation and ion environment will be unique. Identification is also more certin if isotopic analogues are present to permit known pairs of species identified as M+1 and M+2 analogues for qualitative certainty as well.

A known amount of the isotopically enriched species added to the sample and/or equilibrated in solid phase before or during extraction to perform the essential calibration steps required here expressed with the unquantified analyte in the sample. The direct mathematical calculation is the only reliable way to both identify and quantify the analytes(s) as calibration in the traditional sense is not applicable. This is an extension of SIDMS and IDMS as new species are created from the parent species added to the sample and new algorithms are required to directly qualitatively and quantitatively process the analyte.

Microwave-Enhanced Equilibrium

Equilibration Time Effects on Species Using IDMS and SIDMS Methods: Comparison of Conventional Heat, Ultrasound Extraction and Microwave-Enhanced Equilibration In this demonstration, NIST standard reference materials (River sediment SRM 2704 and soil SRM 2711) and European IAEA CRM (human hair IAEA-085) were used in mercury speciation by SIDMS and IDMS techniques. Both SRMs (2704 and 2711) were spiked with known amount of isotopically enriched inorganic mercury ($^{199}Hg^{2+}$). The sample preparation methods evaluated during this study were EPA Method 3052, EPA Draft Method 3200 (Microwave-Assisted Extraction, MAE) and EPA Method 3200 (Ultrasound-Assisted Extraction, UAE). For EPA Method 3052 and Method 3200 (MAE) implementation, the samples were spiked and immediately extracted or digested according to the method. But for Method 3200 (UAE) option, samples were spiked and equilibrated for different amounts of time (1, 3, 6, 12, 24 and 48 h) and then extracted according to this method.

TABLE 6

Equilibration time effects on IDMS analysis of total mercury.

| Sample Preparation Method | Equilibration Time (h) | IDMS Analysis (% Recovery) | |
|---|---|---|---|
| | | SRM 2704 | SRM 2711 |
| Method 3052 (600 s) | N/A | 109 ± 4 | 109 ± 3 |
| Method 3200 (MAE, 600 s) | N/A | 103 ± 4 | 106 ± 2 |
| Method 3200 (UAE) | 1 | 81 ± 12 | 82 ± 4 |
| | 3 | 82 ± 15 | 71 ± 9 |
| | 6 | 93 ± 19 | 75 ± 5 |
| | 12 | 86 ± 14 | 76 ± 2 |
| | 24 | 109 ± 17 | 78 ± 5 |
| | 48 | 102 ± 9 | 77 ± 3 |

Uncertainties are at 95% CI, n = 4.
N/A—not applicable, samples were spiked and immediately digested/extracted.

Since EPA Methods 3052 and 3200 (MAE) are highly efficient, 100% recovery of the total mercury from the two studied SRMs were achieved (Table-6). In this case, the spiked isotope was equilibrated with the sample isotope during extraction/digestion in less than 10 minutes.

Since EPA Method 3200 (UAE) is less efficient in extraction and equilibration of inorganic mercury, the percent recovery is different for the different studied SRMs and with time. The percent recovery for SRM 2704 rose to approximately 100% in 24 hours and no quantitative recovery of SRM 2711 was obtained even after 48 hours. The percent recovery data from Method 3200 (UAE) showed that whether equilibration of the spike with sample takes place for 1 h or 48 h, recovery depends on the sample matrix when using UAE. This reduction-to-practice study conclusively shown that "equilibration of spike isotope with the sample isotope" used for IDMS analysis of aqueous samples does not hold true for complex or solid samples under all types of extraction protocols. In the previously mentioned (Lu Yang, et. al.) chromium species analysis of yeast, this same time dependent extraction over a 12 hours period is experienced for convection and conduction heating of tissue samples. For solid samples, an efficient extraction and equilibration method is necessary for the species of interest prior to mass spectrometry. An inefficient method for extraction and/or digestion and equilibration of solid samples will result inaccurate IDMS or SIDMS analyses.

SIDMS requires equilibration of multiple species simultaneously and the identification of species conversion in order to correct for the final concentrations of each species. Using mercury species in human hair as an example of a good model that only contains methylmercury and inorganic mercury species, the two alternative methods from EPA Method 3200 are compared for extraction of these species using MAE and UAE. In the comparison in Table 7, it can be seen that the UAE does not achieve the correct certified result because the extraction and equilibration combined in this step for the natural and enriched isotopic species does not occur or is not complete enough to obtain the correct answer. This is contrasted by the MAE that uses microwave to extract both species and to equilibrate the enriched isotope species simultaneously. The MAE obtains the certified value within statistical significance in less than half the time of the UAE example.

TABLE 7

Concentration and deconvoluted percent transformation of mercury species in hair sample (IAEA-085) by EPA Method 6800, SIDMS using enriched isotopic reagents and deconvolution algorithms

| Extraction Method | $Hg^{2+}$ (µg/g) | $MeHg^+$ (µg/g) | Total Mercury (µg/g) | $Hg^{2+}$ to $MeHg^+$ (%) | $MeHg^+$ to $Hg^{2+}$ (%) |
|---|---|---|---|---|---|
| Certified value | 0.3 | 22.9 ± 1.0 (100 ± 4)* | 23.2 ± 0.8 (100 ± 3) | — | — |
| Method 3200 (MAE) | 0.59 ± 0.22 | 23.65 ± 1.42 (103 ± 6) | 24.24 ± 1.44 (105 ± 6) | 4 ± 2 | 6 ± 1 |
| Method 3200 (UAE) | 1.13 ± 0.25 | 19.80 ± 1.25 (87 ± 6) | 20.93 ± 1.28 (90 ± 6) | 9 ± 3 | 0 ± 1 |

Uncertainties are at 95% CL, n = 4
MAE—Microwave-assisted extraction, 10 minutes total
UAE—Ultrasound-assisted extraction, 28 minutes total
*values in parentheses represents the percent recovery Poly-Species Transformations and Direct Mathematical Determinations is Required and Superior to Calibration Curves:

It is necessary to evaluate the multiple species transformation and the conversion of multiple species to demonstrate the robustness of the extraction and equilibration method described in this invention. At the present time, there is no tissue sample certified for three mercury species, so the previous certified reference material (human hair CRM, IAEA-085) was spiked with a third mercury species, ethylmercury. This is a logical choice as ethylmercury is indicated in the literature to be the human metabolized mercury species from thimerosal, the mercury preservative in vaccines. With these three species present, there are six species conversions that must be calculated. A mathematical algorithm has been developed for this particular purpose and used for SIDMS measurements of three species and conversions among them during sample preparation. In Table 8, the conversion of over 80% of ethylmercury is revealed primarily due to ethylmercury converting to inorganic mercury and ethylmercury converting to methylmercury. Methylmercury is also significantly converted and is distinctly measured independently from the methylmercury derived from the ethylmercury conversion. This measurement would be impossible without integrated extraction and equilibration of all mercury species simultaneously.

TABLE 8

Human hair CRM (IAEA-085) certified for total mercury and methylmercury, and spiked with natural ethylmercury at a concentration of 22 µg/g. EPA Method 6800 was applied for three species and for all six conversions of species correction using microwave extraction and HPLC-ICP-MS analysis. Multiple replicates are shown along with analytical blank values that were obtained in this reduction-to-practice study.

Sample Identification

| | Analysis Replicates | µg/g Deconvoluted Concentration Hg2+ | µg/g MeHg+ | µg/g EtHg+ | Hg2+ to MeHg+ | MeHg+ to Hg2+ | MeHg+ to EtHg+ | EtHg+ to MeHg+ | EtHg+ to Hg2+ | Hg2+ to EtHg+ |
|---|---|---|---|---|---|---|---|---|---|---|
| Hair-10 | 1 | 0.218 | 21.9816 | 22.2375 | 8.866% | 5.08% | 0.93% | 7.11% | 77.77% | 1.54% |
| IAEA-085 | 2 | 3.216 | 21.3193 | 19.3977 | 9.045% | 6.07% | 1.85% | 7.97% | 81.10% | 1.10% |
| | 3 | 0.937 | 21.5255 | 22.0858 | 6.743% | 6.97% | 2.02% | 6.44% | 78.50% | 1.05% |
| | 4 | 0.817 | 22.3988 | 22.5879 | 9.512% | 4.03% | 1.31% | 7.80% | 77.47% | 0.64% |
| | Average | 1.297 | 21.806 | 21.5772 | 8.54% | 5.54% | 1.53% | 7.33% | 78.71% | 1.08% |
| | Stdev | 1.317448 | 0.482319 | 1.4682 | 1.23% | 1.27% | 0.50% | 0.70% | 1.65% | 0.37% |
| | 95% CL | 2.094742 | 0.766887 | 2.3344 | 1.95% | 2.02% | 0.79% | 1.12% | 2.63% | 0.58% |
| Hair-11 | 1 | 1.357 | 21.6702 | 20.1699 | 9.431% | 5.06% | 1.98% | 6.66% | 67.93% | 1.98% |
| IAEA-085 | 2 | 1.821 | 22.7000 | 20.0567 | 7.112% | 5.50% | 1.70% | 5.44% | 71.10% | 1.22% |
| | 3 | 1.226 | 22.7488 | 20.3397 | 7.756% | 6.15% | 2.10% | 6.30% | 71.32% | 0.47% |
| | 4 | 0.792 | 22.1472 | 21.9031 | 7.857% | 4.04% | 1.98% | 6.55% | 69.32% | 1.69% |
| | Average | 1.299 | 22.317 | 20.6174 | 8.04% | 5.19% | 1.94% | 6.24% | 69.92% | 1.34% |
| | Stdev | 0.423884 | 0.510035 | 0.8650 | 0.98% | 0.89% | 0.17% | 0.55% | 1.60% | 0.66% |
| | 95% CL | 0.673975 | 0.810956 | 1.3754 | 1.57% | 1.41% | 0.27% | 0.87% | 2.54% | 1.05% |
| BLK-111 | 1 | 0.001 | 0.0024 | 0.0079 | 37.672% | 2.77% | 0.98% | 23.10% | 37.90% | 1.68% |
| Blank | 2 | 0.001 | 0.0003 | 0.0068 | 34.121% | 2.25% | 0.44% | 20.58% | 39.57% | 1.76% |
| | 3 | 0.000 | 0.0011 | 0.0026 | 24.773% | 2.75% | 0.36% | 15.69% | 45.88% | 0.85% |
| | 4 | 0.009 | −0.0009 | −0.0023 | 33.687% | 2.18% | 0.35% | 20.67% | 41.25% | 0.61% |
| | Average | 0.002 | 0.001 | 0.0037 | 32.56% | 2.49% | 0.53% | 20.01% | 41.15% | 1.23% |
| | Stdev | 0.004152 | 0.001418 | 0.0046 | 5.49% | 0.32% | 0.30% | 3.11% | 3.44% | 0.58% |
| | 95% CL | 0.006602 | 0.002254 | 0.0074 | 8.73% | 0.51% | 0.48% | 4.94% | 5.47% | 0.92% |
| BLK-121 | 1 | 0.005 | 0.0012 | 0.0010 | 36.138% | 2.30% | 0.42% | 22.76% | 39.33% | 1.58% |
| Blank | 2 | 0.003 | 0.0012 | 0.0010 | 30.392% | 2.46% | 0.66% | 18.25% | 44.02% | 1.41% |
| | 3 | 0.003 | −0.0007 | 0.0014 | 32.475% | 2.85% | 0.50% | 20.61% | 43.03% | 1.61% |
| | 4 | 0.004 | 0.0004 | 0.0011 | 32.846% | 2.55% | 0.53% | 20.46% | 42.24% | 1.53% |
| | Average | 0.004 | 0.001 | 0.0011 | 32.96% | 2.54% | 0.53% | 20.52% | 42.16% | 1.53% |
| | Stdev | 0.000817 | 0.000879 | 0.0002 | 2.38% | 0.23% | 0.10% | 1.84% | 2.02% | 0.08% |
| | 95% CL | 0.001298 | 0.001397 | 0.0003 | 3.78% | 0.37% | 0.16% | 2.93% | 3.21% | 0.13% |

These data are the first application of three species simultaneously correcting for transformations of all three species and intermediate species using microwave extraction (EPA Method 3200) in combination with IDMS/SIDMS (EPA Method 6800) technology demonstrating that even if more than 80% of the ethylmercury may be transformed or destroyed, accurate, rapid, simultaneous measurement is possible only through the application of the SIDMS technology. These measurements are demonstrated and reduced to practice with accuracy maintained at less than 4%.

Algorithms in IDMS and SIDMS are easily adjustable, manually or dynamically, depending on the expression of the species and isotope enriched species. However, calibration curves are not adjustable. They have to be produced each time, routinely and relatively frequently. Calibration curves are not mathematically viable alternatives to multiple species' analyses as errors and shifts prevent their use when even the slightest matrix sample changes are made. Thus, the only mathematically accurate method to make IDMS and SIDMS measurements of isotopically enriched analogues for quantitation. This is critical for homeland security and homeland defense applications and quality assurance measurements where the lowest false positives and false negatives must be obtained and assured. These aspects of IDMS and SIDMS are further described in this document through reduction-to-practice examples.

Section III—Integration in a Fully Automated System Described for Use in the Field: For Example in Homeland Defense and Homeland Security is Described Below:

With the threat of terrorism and potential of purposeful contamination of food, air and drinking water, comes the need for rapid detection of fugitive agents, for a wide range of relatively uncommon, yet very toxic compounds in the most accurate way possible (very low or no false positives). Since the most dangerous agents are very potent, it is highly desirable that the toxin-detector is able to detect at the lowest concentration level, accurately and reliably. Given the mission-critical and time-critical nature of the task, the cycle time (sample pick up, sample preparation/manipulation and analysis) must be in done rapidly, dependently in a rugged field-deployable system capable of maintaining its accuracy and sensitivity under many different situations and environments.

If standards are used it is desirable also desirable not to handle the standards (which will typically be chemical analogues of highly toxic materials), so that these standards are secured in solid phase filters, columns full of beads, cartridges and other small relatively safe solid phase devices that can be transported far more safely than liquids and at concentrations where solutions would be unstable and need to be replaced frequently. If a sample taken in the field or a remote location needed to be transported to a laboratory, the ability to take the sample into a solid phase container, possibly immobilized in a form that will be stable (will keep its chemical form) and safe to handle throughout the chain of custody (the steps between removing a sample from the source and delivery to the point of analysis, typically a specialized laboratory.

Most sensitive and useful detection systems available today employ standard calibration methods in order to establish a useful detector signal range and rely on the calibrated range as a reference to calculate the detector signal produced by the detector when a sample is analyzed. Any chemist who worked in a laboratory would be highly familiar with the use of calibration curves. Unfortunately, calibration curves suffer from a long list of potential sources of errors and require frequent interruption of sample analysis cycles for re-calibration. Matrix (the material the analyte of interest was found in) changes, variations in analyte extraction processes all introduce errors in measurements based on calibration curves. Further, mass spectrometers, the most sensitive detectors capable of detecting molecules at "parts per trillion" levels, produce a signal that drift that invalidates the last established calibration curve. Establishing a new calibration curve, for mass spectrometers, means a number of manual, tedious, time-consuming sample preparation and analysis steps by the analyst. All of these potential sources of errors associated with calibration curves preclude the possibility of automating existing mass spectrometers for homeland security and homeland defense purposes.

Previous inventions and patents associated with IDMS and SIDMS, included earlier in this document by reference, and the invention described in this document, address these problems. The use of enriched isotope tags and enriched standard analogues provide the ability to make measurements at the nuclear realm, rather than the chemical realm that is the technological based of all popular chromogenic, fluorogenic, chemiluminescence and other visualization techniques. This, in turn eliminates many interference and stability problems. IDMS and SIDMS utilize a mathematical solution to produce the final data which eliminates the need for calibration curves, eliminate or minimize problems associated with matrix changes and analyte recovery after extraction steps. The analytical data produced by a mass spectrometer under IDMS and/or SIDMS protocols is a calibrated and highly accurate result. At the time of this patent application, the IDMS and SIDMS protocols were accepted by the US Environmental Protection Agency (EPA) as a national method under the designation, "Method 6800," which has been recognized in by the EPA and British Standards Institute (BSI) in published comments and documents as the only method capable of producing legally-defensible data for speciated elemental analysis.

Currently, preparation of sample prior to analysis (front-end of the process) require sample removal from the site, extraction of the analyte(s) of interest, separation of analyte(s), spiking (or tagging) with an enriched isotope that involve a series of manual steps done by a highly skilled analysts. This process will take anywhere between several hours to several days. Significant shortening of the time and elimination of manual steps from the front-end is imperative before IDMS and SIDMS can be automated. This invention precisely delivers these front-end performance improvements to enable full, turn-key automation.

At the time of this patent application, the inventors were in the process of developing, on behalf of the US government, a five-phase program called "Integrated Instrument-Method System (IIMS)," aimed to create a chemical and biological measurement system that can be field deployed by the armed services and emergency first responders. The self-calibrating, field-deployable is a conceived as a mass analyzer that includes all of the automation features described in this invention.

Whether introduced into the environment by terrorists or by industrial processes, toxic agents exist in speciated and complex chemical forms that frequently make them impossible to detect and measure in an automated fashion with existing laboratory analyses. Typically, long, tedious sample preparation and calibration steps and multiple detection schemes have to be utilized. These schemes are completely unsuitable for an IIMS type of application.

Most or all aspects of the automation requirements, and safety and detection performance issues, have been reduced to practice. For example, the IDMS and SIDMS products, marketed by Applied Isotope Technologies (AIT) have been sold to environmental laboratories, research laboratories, industrial laboratories and Centers for Disease Control for the measurement of water, soil, hair, tissue, blood and urine analysis for toxic chemicals of natural and industrial origins. AIT products have been sold as IDMS and SIDMS kits that includes isotopic spikes, enriched standard analogues and software for the final mathematical deconvolution and calculation. AIT's products have been used in different types of mass spectrometers, such as Time-of-Flight (TOF) and Inductively Coupled Plasma (ICP), coupled to High Performance Liquid Chromatography (HPLC) and Gas Chromatography (GC), using both electrospray ionization (liquid-to-liquid spray) and gas ionization (liquid-to-gas) forms. Additional inventions, such as solid-phase media holding isotopic tags or enriched standard analogues, used for rapid spiking and equilibration, and simultaneous extraction, spiking and equilibration have been reduced to practice.

The invention claimed is:

1. A method for equilibrating an isotope dilution mass spectrometry sample, comprising the steps of:
    a) adding to a solid phase carrier selected from the group consisting of surface modified and/or functionalized ion exchange medium, a surface-modified solid phase support, an adsorption medium, a solid phase extraction medium, a resin bonded solid phase, sorbents, solid and/or porous beads, palicular and surface activated beads, mixed-bed media, filters, dual-state liquids used for immobilized liquid extraction, fibers packaged in packed columns, a surface-modified SELDI plate, a solid phase surface modified plate, surface-modified filters, solid-phase extraction cartridges and immunoassay solid phase media carriers a quantity or concentration of an isotopically tagged analyte analogue and immobilizing through adsorption or chemical attachment said isotopically tagged analyte analogue on said solid phase carrier;
    b) further adding to said solid phase carrier having the immobilized isotopically tagged analyte analogue from step a), a sample containing or suspected to contain an analyte of interest corresponding to said isotopically tagged analyte analogue and holding the sample on said solid phase carrier;

c) conducting an equilibration step by incubating the solid phase carrier from step b) with said sample for between 1 second and 24 hours to make an equilibrated sample containing isotopically tagged analyte analogue; and d) subjecting said equilibrated sample containing said isotopically tagged analyte analogue to direct ionization and transport into a mass spectrometer for analysis.

2. The method according to claim 1 wherein said isotope dilution mass spectrometry sample is a speciated isotope dilution mass spectrometry sample.

3. The method according to claim 1 wherein said isotope dilution mass spectrometry sample is a species specific isotope dilution mass spectrometry sample.

4. The method according to claim 1 wherein said step of incubating the solid phase carrier and the sample accomplishes equilibration in a time period between 1 and 600 seconds.

5. The method according to claim 1 wherein the analyte is selected from the group consisting of compounds or compositions containing any element for which isotopic variation occurs in nature.

6. The method according to claim 5 wherein the analyte is selected from the group consisting of compounds or compositions containing mercury, tert-butanol, methyl-t-butyl ether, ethyl-t-butyl ether, diisopropyl ether, t-amylmethyl ether, morphine, dioxane, dichloroethane, tetrachlorethane, naphthalene, and phenanthrene.

7. The method according to claim 5 wherein the concentration of analyte in the sample is calculated based on the ratio of the total analyte present as determined by mass spectrometry to the isotopically tagged analyte analogue.

8. The method according to claim 5 wherein the analyte concentration is directly calculated using a mathematical calculation of concentration and/or degradation adjustment based on isotope ratios of species without application of a calibration curve.

9. The method according to claim 5 wherein solid phase equilibration is used to automate IDMS and/or SIDMS mass spectrometry.

10. A method for equilibrating an isotope dilution mass spectrometry sample, comprising the steps of:

a) adding to a solid phase carrier selected from the group consisting of surface modified and/or functionalized ion exchange medium, a surface-modified solid phase support, adsorption medium, solid phase extraction medium, a resin bonded solid phase, sorbents, solid and/or porous beads, palicular and surface activated beads, mixed-bed media, filters, dual-state liquids used for immobilized liquid extraction, fibers packaged in packed columns, a surface-modified SELDI plate, a solid phase surface modified plate, surface-modified filters, solid-phase extraction cartridges and immunoassay solid phase media carriers a quantity or concentration of a sample containing or suspected to contain an analyte of interest corresponding to an isotopically tagged analyte analogue and immobilizing said sample on said microtiter plate or said surface modified solid phase support through adsorption or chemical attachment;

b) further adding to said solid phase carrier having the immobilized sample containing or suspected to contain said analyte of interest from step a), a quantity of said isotopically tagged analyte analogue and immobilizing said isotopically tagged analyte analogue on said solid phase carrier;

c) conducting an equilibration step by incubating the solid phase carrier, said isotopically tagged analyte analogue and said sample from step b) for between 1 second and 24 hours to make an equilibrated sample containing isotopically tagged analyte analogue; and d) subjecting said equilibrated sample containing said isotopically tagged analyte analogue to direct ionization and transport into a mass spectrometer for analysis.

* * * * *